US009427728B2

(12) United States Patent
Sidheswaran et al.

(10) Patent No.: US 9,427,728 B2
(45) Date of Patent: Aug. 30, 2016

(54) USE OF MANGANESE OXIDE AND ACTIVATED CARBON FIBERS FOR REMOVING A PARTICLE, VOLATILE ORGANIC COMPOUND OR OZONE FROM A GAS

(71) Applicant: The Regents of the University of California, Oakland, CA (US)

(72) Inventors: Meera A. Sidheswaran, Kingsport, TN (US); Hugo Destaillats, Scottsdale, AZ (US); William J. Fisk, Oakland, CA (US)

(73) Assignee: The Regents of The University of California, Oakland, CA (US)

( * ) Notice: Subject to any disclaimer, the term of this patent is extended or adjusted under 35 U.S.C. 154(b) by 3 days.

(21) Appl. No.: 14/092,829

(22) Filed: Nov. 27, 2013

(65) Prior Publication Data

US 2014/0255283 A1 Sep. 11, 2014

Related U.S. Application Data

(63) Continuation of application No. PCT/US2012/040807, filed on Jun. 4, 2012.

(60) Provisional application No. 61/493,375, filed on Jun. 3, 2011.

(51) Int. Cl.
*B01J 23/34* (2006.01)
*B01J 37/03* (2006.01)
(Continued)

(52) U.S. Cl.
CPC ........ *B01J 23/34* (2013.01); *A61L 9/00* (2013.01); *B01D 53/8668* (2013.01); *B01J 20/20* (2013.01);
(Continued)

(58) Field of Classification Search
CPC ............ B01J 23/34; B01J 20/20; A61L 9/00
USPC ....... 423/245.1, 605; 502/324, 416; 422/122
See application file for complete search history.

(56) References Cited

U.S. PATENT DOCUMENTS 3,819,334 A * 6/1974 Yoshida et al. ............... 422/173
2008/0311031 A1* 12/2008 Vitner et al. .................. 423/604
2010/0296966 A1* 11/2010 Bae et al. .......................... 422/4

OTHER PUBLICATIONS

Lahousse et al., Evaluation of gamma-MnO2 as a VOC removal catalyst: comparison with a noble metal catalyst, 1998, Journal of Catalysis, 178, 214-225.*

(Continued)

*Primary Examiner* — Matthew E Hoban
*Assistant Examiner* — James Fiorito
(74) *Attorney, Agent, or Firm* — Weaver Austin Villeneuve & Sampson LLP

(57) ABSTRACT

The present invention provides for a device for reducing a volatile organic compound (VOC) content of a gas comprising a manganese oxide ($MnO_x$) catalyst. The manganese oxide ($MnO_x$) catalyst is capable of catalyzing formaldehyde at room temperature, with complete conversion, to $CO_2$ and water vapor. The manganese oxide ($MnO_x$) catalyst itself is not consumed by the reaction of formaldehyde into $CO_2$ and water vapor. The present invention also provides for a device for reducing or removing a particle, a VOC and/or ozone from a gas comprising an activated carbon filter (ACF) on a media that is capable of being periodically regenerated.

11 Claims, 15 Drawing Sheets

(51) Int. Cl.
| | |
|---|---|
| B01J 21/18 | (2006.01) |
| B01D 53/86 | (2006.01) |
| B01J 35/00 | (2006.01) |
| B01J 35/06 | (2006.01) |
| B01J 35/10 | (2006.01) |
| B01J 37/02 | (2006.01) |
| C09D 1/00 | (2006.01) |
| A61L 9/00 | (2006.01) |
| B01J 20/20 | (2006.01) |
| B01J 35/04 | (2006.01) |

(52) U.S. Cl.
CPC .............. *B01J 21/18* (2013.01); *B01J 35/002* (2013.01); *B01J 35/006* (2013.01); *B01J 35/06* (2013.01); *B01J 35/1009* (2013.01); *B01J 35/1019* (2013.01); *B01J 37/0215* (2013.01); *B01J 37/031* (2013.01); *C09D 1/00* (2013.01); *B01D 2253/102* (2013.01); *B01D 2255/2073* (2013.01); *B01D 2257/106* (2013.01); *B01D 2257/708* (2013.01); *B01J 35/04* (2013.01)

(56) References Cited

OTHER PUBLICATIONS

Lawrence Berkeley National Laboratory, Technology Transfer and Intellectual Property Management, "Energy saving system to remove volatile organic compounds (VOCs) from indoor air," http://www.lbl.gov/tt/techs/lbnl2970.html, posted to TTIPM on Aug. 8, 2011.
Sidheswaran, Meera A. et al., "Active and passive methods for indoor formaldehyde elimination."
Ahmed, Khalid Abdelazez Mohamed et al., "$Mn_3O_4$ nanoplates and nanoparticles: synthesis, characterization, electrochemical and catalytic properties," Journal of Solid State Chemistry 183 (2010) 744-751.
Attenburrow, J. et al., "A synthesis of vitamin A from cycloHexanone," Research and Development Division, Glaxo Laboratories, Ltd., published Jan. 1, 1952.
Baltanas, Miguel A., "Development of supported manganese oxides for partial oxidation: co oxidation and oxygen availability," Applied Catalysis, 20 (1986) 15-29.
Benne, K. et al., "Assessment of the energy impacts of outside air in the commercial sector," US Department of Energy, National Renewable Energy Laboratory, technical report NREL/TP-550-41955, Apr. 2009.
Bish, David L. et al., "Thermal behavior of complex, tunnel-structure manganese oxides," American Mineralogist, vol. 74, pp. 177-186, 1989.
Brooks, C.S. et al., "Reaction of hydrogen with a nonstoichiometric manganese dioxide," Journal of Catalysis 4, 535-545 (1965).
Brooks, C.S. et al., "The kinetics of hydrogen and carbon monoxide oxidation over a manganese oxide," Journal of Catalysis 8, 272-282 (1967).
Cellier, Caroline et al., "Extent of the participation of lattice oxygen from $\gamma$-$MnO_2$ in VOCs total oxidation: influence of the VOCs nature," Catalysis Today 117 (2006) 350-355.
Chen, Hongmin et al., "Self-assembly of novel mesoporous manganese oxide nanostructures and their application in oxidative decomposition of formaldehyde," J. Phys. Chem. C 2007, 111, 18033-18038.
Chen, Tan et al., "Tunnel structure effect of manganese oxides in complete oxidation of formaldehyde," Microporous and Mesoporous Materials 122 (2009) 270-274.
Chu, Xiujuan et al., "Catalytic decomposition of formaldehyde on nanometer," CCSE Modern Applied Science, vol. 3, No. 4, Apr. 2009.
Cimino, A. et al., "Catalytic activity of $Mn^{3+}$ and $Mn^{4+}$ ions dispersed in MgO for CO oxidation," Journal of Catalysis 33, 493-496 (1974).

Cogliano, Vincent James et al., "Meeting report: Summary of IARC monographs on formaldehyde, 2-butoxyethanol, and 1-tert-butoxy-2-propanol," Environmental Health Perspectives, vol. 113, No. 9, pp. 1205-1208, Sep. 2005.
Destaillats, Hugo et al., "Indoor secondary pollutants from household product emissions in the presence of ozone: a bench-scale chamber study," Environ. Sci. Technol. 2006, 40, 4421-4428.
Doornkamp, C. et al., "The universal character of the Mars and Van Krevelen mechanism," Journal of Molecular Catalysis A: Chemical 162 (2000) 19-32.
Girman, John R. et al., "Developing baseline information on buildings and indoor air quality (BASE '94): Part II—environmental pollutant measurements and occupant perceptions," US Environmental Protection Agency, presented at Healthy Buildings '95, Sep. 11-14, 1995.
Griffith, B. et al., "Methodology for modeling building energy performance across the commercial sector," US Department of Energy, National Renewable Energy Laboratory, technical report NREL/TP-550-41956, Mar. 2008.
Harfenist, M. et al., "The oxidation of allyl and benzyl alcohols to the aldehydes," Research Laboratories of Chas. Pfizer and Co., Apr. 19, 1954.
Hodgson, A.T. et al., "Sources of formaldehyde, other aldehydes and terpenes in a new manufactured house," Indoor Air 2002, 12: 235-242, © US Government.
Hodgson, Alfred T. et al., "Volatile organic compounds in indoor air: a review of concentrations measured in North America since 1990," Lawrence Berkeley National Laboratory, LBNL-51715, Apr. 21, 2003.
Kobayashi, Masayoshi et al., "Distribution of oxidation power of surface oxygen species on manganese dioxide during the oxidation of carbon monoxide," Journal of Catalysis 21, 48-55 (1971).
Kobayashi, Masayoshi et al., "Application of transient response method to the study of heterogeneous catalysis," Journal of Catalysis 27, 100-107 (1972).
Maddalena, Randy et al., "Formaldehyde and other volatile organic chemical emissions in four FEMA temporary housing units," Environ. Sci. Technol. 2009, 43, 5626-5632.
Mendell, M.J., "Indoor residential chemical emissions as risk factors for respiratory and allergic effects in children: a review," Indoor Air 2007, 17: 259-277, © 2007 Blackwell Munksgaard.
National Institute for Occupational Safety and Health (1992) "NIOSH RELs and general recommendations for safety and health," DHHS (NIOSH) publication No. 92-100, http://www.cdc.gov/niosh/pdfs/92-100-c.pdf.
Post, Jeffrey E., "Manganese oxide minerals: crystal structures and economic and environmental significance," Proceedings of the National Academy of Sciences of the United Stat4es of America 96 (7): 3447-3454.
Prasad, V.S. et al., "Removal of bacteria and turbidity from water by chemically treated manganese and iron ores," J. Water SRT—Aqua, vol. 44, No. 2, pp. 80-82, 1995.
Sekine, Yoshika et al., "Removal of formaldehyde from indoor air by passive type air-cleaning materials," Atmospheric Environment 35(11): 2001-2007.
Sekine, Yoshika, "Oxidative decomposition of formaldehyde by metal oxides at room temperature," Atmospheric Environment 36 (35): 5543-5547.
Sidheswaran, Meera et al., "New air cleaning strategies for reduced commercial building ventilation energy—FY11 final report," Ernest Orlando Lawrence Berkeley National Laboratory, LBNL-5264E, Oct. 2011.
Sidheswaran, Meera et al., "New air cleaning strategies for reduced commercial building ventilation energy," Oct. 27, 2010, Lawrence Berkeley National Laboratory publication, paper LBNL-4026E, published Dec. 9, 2010.
Singer, B.C. et al., "Cleaning products and air fresheners: emissions and resulting concentrations of glycol ethers and terpenoids," Indoor Air 2006, 16: 179-191, © The Authors.
Tang, Xingu et al., "$MnO_x$-$CeO_2$ mixed oxide catalysts for complete oxidation of formaldehyde: effect of preparation method and calcination temperature," Applied Catalysis B-Environmental 62 (3-4): 265-273.

(56) References Cited

OTHER PUBLICATIONS

Tang, Xingfu et al., "Pt/MnO$_x$-CeO$_2$ catalysts for the complete oxidation of formaldehyde at ambient temperature," Applied Catalysis B-Environmental 81 (2008) 115-121.

Tang, Xingfu et al., "Significant enhancement of catalytic activities of manganese oxide octahedral molecular sieve by marginal amount of doping vanadium," Catalysis Communications 11 (2010) 871-875.

United States Environmental Protection Agency, "A standardized EPA protocol for characterizing indoor air quality in large office buildings," Feb. 2003.

Wen, Yiran et al., "Impact of synthesis method on catalytic performance of MnO$_x$-SnO$_2$ for controlling formaldehyde emission," Catalysis Communications 10 (2009) 1157-1160.

Xu, Qiujian et al., "Research of formaldehyde removal by room temperature thermo-catalytic oxidation reactor," Proceedings of Indoor Air, Copenhagen, Denmark, Paper ID: 692, Aug. 2008.

Yuan, Jikang et al., "Shape-controlled synthesis of manganese oxide octahedral molecular sieve three-dimensional nanostructures," J. Am. Chem. Soc. 2005, 127, 14184-14185.

Yuan, Jikang et al., "Self-assembly of microporous manganese oxide octahedral molecular sieve hexagonal flakes into mesoporous hollow nanospheres," J. Am. Chem. Soc. 2003, 125, 4966-4967.

Zhong, Liang-Shu et al., "Self-assembled 3D flowerlike iron oxide nanostructures and their application in water treatment," Adv. Mater. 2006, 18, 2426-2431.

Zwicker, W.K. et al., "Nsutite—a widespread manganese oxide mineral," The American Mineralogist, vol. 47, Mar.-Apr. 1962.

\* cited by examiner

USE OF MANGANESE OXIDE AND ACTIVATED CARBON FIBERS FOR REMOVING A PARTICLE, VOLATILE ORGANIC COMPOUND OR OZONE FROM A GAS

CROSS-REFERENCE TO RELATED APPLICATIONS

This application claims priority as a continuation application to PCT International Patent Application No. PCT/US2012/40807, filed Jun. 4, 2012, which claims priority to U.S. Provisional Patent Application Ser. No. 61/493,375, filed Jun. 3, 2011, both of which are hereby incorporated by reference in their entireties.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of reducing gas pollutants.

BACKGROUND OF THE INVENTION

Manganese dioxide ($MnO_2$) is a relatively abundant and inexpensive metal oxide. Manganese oxide-based nanoparticles have been used for water purification for a long time (Prasad and Chaudhuri 1995). The redox properties of manganese oxide minerals make them useful catalysts in industrial processes. Naturally occurring manganese oxides have a $MnO_6$ octahedron structure that assembles into a large variety of structural arrangement, yielding minerals with high surface area. Also, multiple oxidation states of Mn atoms in a single mineral facilitate catalysis of oxidation reactions (Post 1999). A great deal of attention has been placed recently on the synthesis of novel $MnO_2$-based catalysts for the removal of formaldehyde and other volatile organic compounds (VOCs) at room or low temperatures (<100° C.) (Sekine 2002; Xu et al. 2008). Xu et al. (2008) used the results of bench scale experiments to predict airborne formaldehyde removal efficiency of coated honeycomb substrates with various dimensions, indicating that up to 20% formaldehyde removal efficiency could be obtained with very low pressure drops (about 2 to 3 Pa) operating at face velocities typical of air filtering systems (1-3 m s$^{-1}$). In addition to active air cleaning applications, there is some additional evidence of Mn-based catalyst efficacy in passive applications. In a residential setting, deployed manganese oxide within wallboard was reported to reduce 50% to 80% of indoor formaldehyde levels throughout a 7-month long study period (Sekine and Nishimura 2001).

Doping of $MnO_2$ with other transition metals and synthesis of mixed oxides showed improved formaldehyde removal efficiencies. For example, $MnO_x$—$CeO_2$ catalysts had improved performances than $MnO_2$ synthesized by the same method (Tang et al. 2006; Tang et al. 2008). Also, other authors showed good performance of manganese oxides doped with other transition metals, such as vanadium (Tang et al. 2010) and tin (Wen et al. 2009). Several manganese oxide nano and meso structures (e.g., pyrolusite, cryptomelane) have been shown to have very high catalytic activity in the complete oxidation of formaldehyde (yielding $CO_2$ and $H_2O$) at low temperatures, explained by its porosity, degree of crystallinity, reducibility and average oxidation state of the manganese atoms (Chen et al. 2009). Further, nano-structured mixed valence oxides (such as $Mn_3O_4$) were shown to effectively catalyze the oxidation of formaldehyde at room temperature (Ahmed et al. 2010). In most of the cases mentioned here, low temperature oxidation of formaldehyde likely takes places via a Mars-van Krevelen (MvK) mechanism, as is usually described for high temperature catalysis, in which lattice oxygen atoms from the catalyst participate in the initial step of the reaction, and are subsequently replenished by reduction of atmospheric $O_2$ (Doornkamp and Ponec 2000; Cellier et al. 2006):

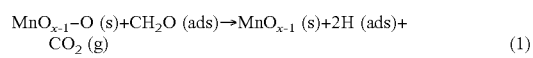

$$MnO_{x-1}-O\ (s)+CH_2O\ (ads) \rightarrow MnO_{x-1}\ (s)+2H\ (ads)+CO_2\ (g) \quad (1)$$

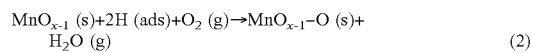

$$MnO_{x-1}\ (s)+2H\ (ads)+O_2\ (g) \rightarrow MnO_{x-1}-O\ (s)+H_2O\ (g) \quad (2)$$

In this mechanism, catalyst efficiency is associated with the number of active surface sites with Mn atoms susceptible to be cyclically reduced and re-oxidized as shown in equations 1 and 2. Formic acid can be formed as a byproduct of incomplete oxidation, and may be found in the gas phase or adsorbed to the catalyst.

Although study exists on the $MnO_2$ catalytic oxidation of formaldehyde there is not enough evidence to support the MvK mechanism. Prior studies also fail to address the issue of implementing this technology successfully to eliminate gaseous formaldehyde at indoor levels.

SUMMARY OF THE INVENTION

The present invention provides for a device for reducing a volatile organic compound (VOC) content of a gas comprising a manganese oxide ($MnO_x$) catalyst. The manganese oxide ($MnO_x$) catalyst is capable of catalyzing formaldehyde, acetaldehyde, and other volatile organic compounds (VOCs) at room temperature, with complete conversion or nearly complete conversion, to $CO_2$ and water vapor. The manganese oxide ($MnO_x$) catalyst itself is not consumed by the reaction of formaldehyde into $CO_2$ and water vapor.

The present invention also provides for a method of preparing the $MnO_x$ catalyst of the invention comprising: providing a manganese salt and a permanganate salt solution wherein the molar ratio of the permanganate to manganese salt has a ratio of about 2:3, forming a black suspension comprising a precipitate, separating the precipitate from the solution, optionally washing the precipitate, heating the precipitate, and optionally converting the precipitate into a powder. The precipitate is manganese oxide ($MnO_x$). In some embodiments of the invention, the heating step comprises heating the precipitate to a temperature equal to or more than about 50° C. In some embodiments of the invention, the heating step comprises heating the precipitate to a temperature equal to or more than about 100° C.

The present invention also provides for a method for reducing a volatile organic compound (VOC) content of a gas, comprising: contacting the gas comprising one or more VOC with a $MnO_x$ catalyst, thereby obtaining a gas having a reduced content in the VOC as compared to the gas before contacting it with the $MnO_2$ catalyst.

The present invention also provides for application of the $MnO_x$ catalyst to a particle filter so that the VOC content of the gas stream passing through the filter is reduced by the catalyst.

The present invention also provides for use of a spray procedure to apply the $MnO_x$ catalyst to a particle filter.

The present invention also provides for a composition useful as a material for coating a building comprising the manganese oxide catalyst; such that when air contacts the composition, the formaldehyde in the air is decomposed. In some embodiments of the invention, the composition is useful for coating the outside/exterior or inside/interior of the building. In some embodiments of the invention, the composition is paint. The manganese oxide catalyst can be added to a paint that is applied to the interior or exterior surfaces of gypsum wall board. Natural air motion will cause air to contact the coated surfaces where catalytic decomposition of formaldehyde can take place. In some embodiments of the invention, the composition is used for coating a surface that is normally visible to an occupant of a building, such the surface of a wall. In such cases, the indoor air contacts a large surface area of catalyst coated material and no fans are needed for air cleaning. In some embodiments of the invention, the catalyst is applied to a particle filter that is then installed in an airstream drawn from a building interior and returned to a building interior.

In some embodiments of the invention, the composition is useful for coating the interior surface of a duct system, or the surfaces of heating and cooling coils. Formaldehyde in air that flows through the ducts or heating or cooling coils can be decomposed and this air, with a reduced formaldehyde concentration can be subsequently supplied to a building's interior. The advantage of coating these non-visible surfaces that contact indoor air is that a large amount of the manganese oxide catalyst can be applied without concerns about producing a visually unattractive surface. In some embodiments of the invention, the composition is used for coating a surface that is not normally visible to an occupant of a building, such the interior surface of a duct.

In some embodiments of the invention, the $MnO_x$ catalyst is used in an integrated system that also comprises a particle filtration system and/or an activated carbon fiber system, and may also include a fan. In this integrated system the particle filtration system removes particles from the gas stream, the $MnO_x$ catalyst destroys formaldehyde, acetaldehyde and other volatile organic compounds (VOCs), and the activated carbon fiber system removes additional volatile organic compounds (VOCs) from the gas stream that are not destroyed by the $MnO_x$ catalyst.

In some embodiments of the invention the $MnO_x$ catalyst is applied to activated carbon fibers, such as to a cloth or other woven media containing activated carbon fibers. In this embodiment the $MnO_x$ catalyst destroys formaldehyde, acetaldehyde and other volatile organic compounds (VOCs), and the activated carbon fiber system removes additional volatile organic compounds from the gas stream that are not destroyed by the $MnO_x$ catalyst.

The present invention also provides for a device for reducing or removing a particle, a volatile organic compound (VOC) and/or ozone from a gas, such as air, comprising an activated carbon filter (ACF) on a media that is capable of being periodically regenerated. The regeneration can be effected by using unheated outdoor air, heated indoor or outdoor air, or by direct electrical resistance heating of the ACF media, with the regeneration gas stream carrying VOCs previously adsorbed on the ACF media to outdoors.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
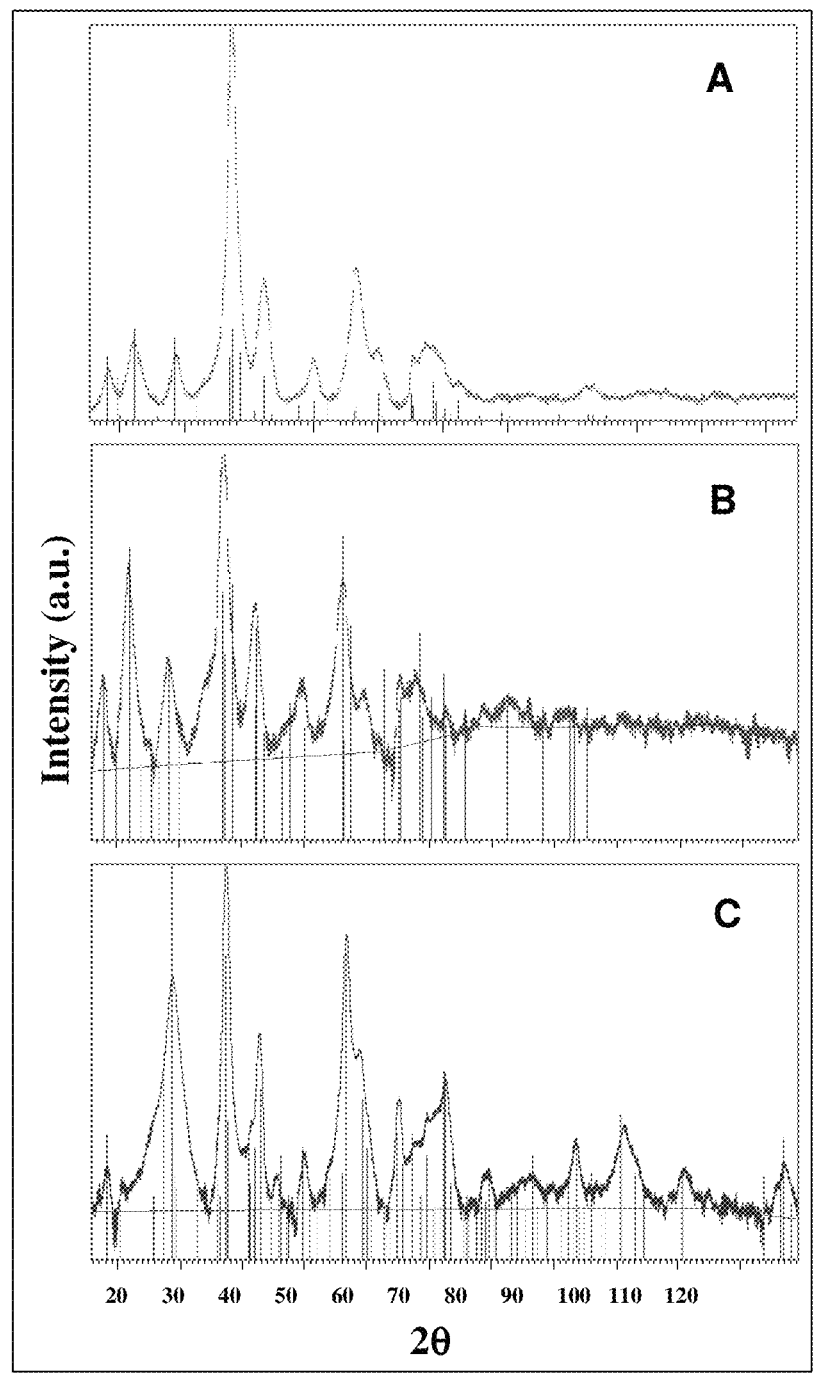
FIG. 1 shows the X-Ray Diffraction spectrum of $MnO_x$ treated at (A) 100° C.; (B) 200° C.; (C) 400° C.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to a "VOC" includes a VOC compound as well as a plurality of VOC compounds, either the same (e.g., the same molecule) or different.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "catalyst", "manganese oxide catalyst", "manganese oxide", or "$MnO_x$" used in describing the present invention means a mixture comprising two or more of the following manganese oxides: $MnO_2$, $MnO$, $Mn^{4+}_{1-x}Mn^{2+}_xO_{2-2x}(OH)_{2x}$, where x=about 0.06 to about 0.07, and $KMn^{4+}_6Mn^{2+}_2O_{16}$. In some embodiments of the invention, the catalyst comprises about 12.20% $MnO$. In some embodiments of the invention, the catalyst comprises about 84.71% $MnO_2$.

The present invention provides for a device for reducing a volatile organic compound (VOC) content of a gas comprising a manganese oxide ($MnO_x$) catalyst. The manganese oxide ($MnO_x$) catalyst is capable of catalyzing formaldehyde at room temperature, with complete or nearly complete conversion, to $CO_2$ and water vapor. The catalyst is also capable of destroying acetaldehyde and acetone and other VOCs. The manganese oxide ($MnO_x$) catalyst itself is not consumed by the reaction of formaldehyde into $CO_2$ and water vapor.

In some embodiments of the invention, the $MnO_x$ catalyst has a BET surface area measurement of equal to or more than about 5 or 10 $m^2$ $g^{-1}$. In some embodiments of the invention, the $MnO_x$ catalyst has a BET surface area measurement of equal to or more than about 50 or 90 $m^2$ $g^{-1}$. In some embodiments of the invention, the $MnO_x$ catalyst has a BET surface area measurement of more than about 100 or 140 $m^2$ $g^{-1}$.

In some embodiments of the invention, the $MnO_x$ catalyst is supported on a heating ventilation and air conditioning (HVAC) particle filter. In some embodiments of the invention, the HVAC filter is about one inch thick.

In some embodiments of the invention the catalyst is supported on activated carbon fibers which may be arranged as a woven media or cloth.

In some embodiments of the invention, the device is an integrated-technology air cleaner (ITAC). In some embodiments of the invention, the device is a residential-size device, such as a residence-size ITAC. In some embodiments of the invention, the device has a size sufficient for cleaning the air of a commercial-building. In some embodiments of the invention, the device further comprises an activated carbon filter (ACF) that is periodically regenerated using unheated outdoor air, heated indoor or outdoor air, or by direct electrical resistance heating of the ACF media, with the regeneration gas stream carrying VOCs previously adsorbed on the ACF media to outdoors. In some embodiments of the invention, the device further comprises a particle filter. In some embodiments of the invention, the device further comprises one or more damper. In some embodiments of the invention, the device further comprises a fan for propelling cleaned gas, such a gas reduced in its VOC content. In some embodiments of the invention, the device comprises the features depicted in FIG. 5 herein.

The present invention also provides for a method of preparing the $MnO_x$ catalyst of the invention comprising: providing a manganese salt and a permanganate salt solution wherein the molar ratio of the permanganate to manganese salt has a ratio of about 2:3, forming a black suspension comprising a precipitate, separating the precipitate from the solution, optionally washing the precipitate, heating the precipitate, and optionally converting the precipitate into a powder. The precipitate is manganese oxide ($MnO_x$).

In some embodiments of the invention, the manganese salt is manganese sulfate ($MnSO_4$). In some embodiments of the invention, the permanganate is sodium permanganate ($NaMnO_4$). In some embodiments of the invention, the providing step comprises dissolving the manganese salt and permanganate salt in distilled water, and optionally adding the sodium permanganate solution was added slowly with constant stirring to the manganese sulfate aqueous solution. In some embodiments of the invention, the forming step comprises incubating the black suspension at room temperature for about 24 hours. In some embodiments of the invention, the separating step comprises filtering the black suspension. In some embodiments of the invention, the washing step comprises washing the precipitate with deionized water for one or more times. The one or more washing steps comprise removing one or more impurities in the precipitate. In some embodiments of the invention, the heating step comprises heating the precipitate in air for at least about 12 hours at a temperature equal to or more than about 100° C. In some embodiments of the invention, the heating step comprises heating the precipitate in air for at least about 12 hours at a temperature equal to or more than about 200° C. In some embodiments of the invention, the heating step comprises heating the precipitate in air for at least about 12 hours at a temperature equal to or more than about 400° C.

In some embodiments of the invention, the manganese oxide is loaded onto a filter, such a particle filter, such as a HVAC particle filter.

The present invention also provides for a method for reducing a volatile organic compound (VOC) content of a gas, comprising: contacting the gas with a $MnO_x$ catalyst, thereby obtaining a gas having a reduced content in the VOC as compared to the gas before contacting it with the $MnO_x$ catalyst. In some embodiments of the invention, the VOC is an aldehyde, such as a $C_1$-$C_{10}$ aldehyde, such as formaldehyde or acetaldehyde.

In some embodiments of the invention, the VOC is toluene, benzene, o-xylene, 1-butanol, limonene, undecane, formaldehyde, or a mixture thereof.

In some embodiments of the invention, the gas is air, such as indoor air. In some embodiments of the invention, the air is air known to comprise a VOC, or is suspected to comprise a VOC.

In some embodiments of the invention, the gas comprises from over zero ppb of the VOC. In some embodiments of the invention, the gas comprises from over zero ppb to about 1,000 ppb of the VOC. In some embodiments of the invention, the gas comprises from about 20 ppb to about 300 ppb of the VOC.

In some embodiments of the invention, the device is capable of reducing the VOC content of a gas by equal to or more than about 10%. In some embodiments of the invention, the device is capable of reducing the VOC content of a gas by equal to or more than about 20%, 30%, 40%, 50%, 60%, or 70%.

In some embodiments of the invention, the device comprises the manganese oxide catalyst, in a particle form, applied to a fibrous particle filter; so that when air passes through the filter, formaldehyde and/or other VOCs in the air are decomposed by the catalyst at room temperature.

In some embodiments of the invention, the device comprises the manganese oxide catalyst, in particle form, applied to a particle filter coated with a viscous tackifier; so that when air passes through the filter, any formaldehyde in the air is decomposed by the catalyst at room temperature. The tackifier applied to the fibrous particle filter helps the catalyst particles adhere to the particle filter.

In some embodiments of the invention, when the manganese oxide catalyst is applied to a particle filter, the device is capable of simultaneously or separately removing particles and/or formaldehyde. In some embodiments of the invention, the catalyst particles are applied to the downstream surface of the particle filter. The downstream surface of the particle filter typically does not become coated with normal airborne particles removed from air by the filter.

In some embodiments of the invention, the device comprises the manganese oxide catalyst, in particle form, applied to an activated carbon fiber cloth; so that when air passes through the activated carbon fiber cloth, any formaldehyde in the air is decomposed by the catalyst at room temperature. The activated carbon fiber cloth, optionally with periodic in-situ regeneration, simultaneously removes a broad spectrum of other indoor VOCs from the air while the catalyst provides enhanced removal of formaldehyde from the air.

In some embodiments of the invention, when the manganese oxide catalyst is applied to an activated carbon fiber cloth, the device is capable of simultaneously or separately removing a broad spectrum of VOCs and formaldehyde. The activated carbon fiber is capable of weakly absorbing formaldehyde.

In some embodiments of the invention, the method comprises depositing the manganese dioxide catalyst, in particle form, on particle filters using a fluidized bed which causes the catalyst particles to be suspended in air when it is drawn through the filter, such that the suspended catalyst particles deposit on the fibrous media of the particle filter.

In some embodiments of the invention, the method comprises providing a suspension comprising the manganese dioxide catalyst, in particle form, and an evaporatable liquid, spraying the suspension onto a particle filter, and optionally evaporating the liquid such that the catalyst particles is deposited on the fibrous media of the particle filter.

Figure 6:
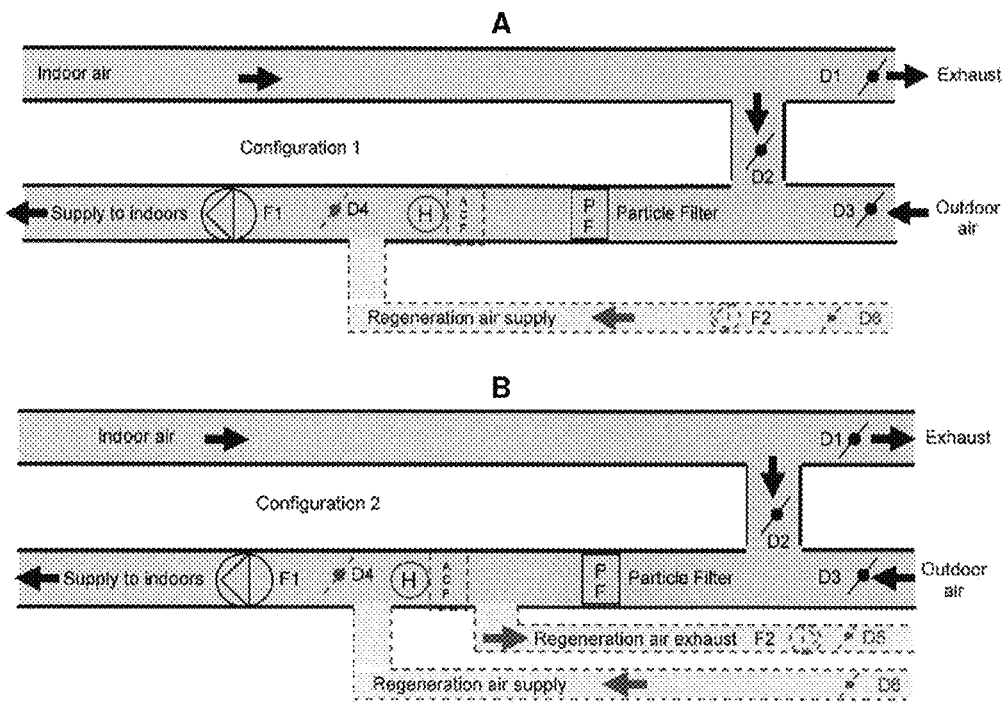
FIG. 6 shows two configurations for activated carbon fiber air cleaning in a commercial HVAC system. Items in red are added when activated carbon fiber air cleaning is used. Panel A shows configuration 1 which requires less hardware. Panel B shows configuration 2 which avoids passing heated high-VOC regeneration air through the particle filter where some VOCs might adsorb and subsequently be released to indoor air. During periods of air cleaning, air passes through the blue shaded airflow paths and VOCs are adsorbed on the activated carbon fiber filter. When the activated carbon fiber filter is regenerated, fan 1 is turned off, fan 2 is turned on, the heater (when used) is turned on, damper 6 (configuration 1) or damper 5 and damper 6 (configuration 2) are opened, damper 2 and damper 4 are closed (configuration 1) or dampers 2-4 are closed (configuration 2), and VOCs are desorbed from the activated carbon fiber filter and vented to outdoors. D1-D6 are dampers wherein D1-D3 are dampers normally found in existing HVAC systems. F1 is the normal supply air fan. F2 is the added regeneration air fan. PF is a normal particle filter. ACF is the added activated carbon fiber filter. H is an optional heater which is needed only when temperatures are increased during regeneration which is required only in devices which comprise the ACF.
Figure 7:
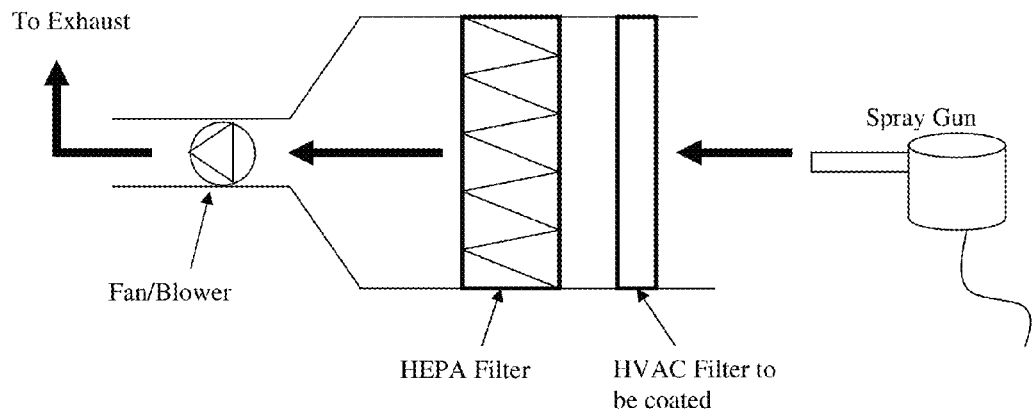
FIG. 7 shows a filter coating mount.

In some embodiments of the invention, the device comprises a configuration shown in FIG. 6. The device comprises a VOC air cleaning using activated carbon fiber (ACF) cloth installed in a heating, ventilating, and air conditioning system, dampers, and a fan and duct system for periodically removing VOCs from the ACF cloth so that it can again be used for VOC air cleaning. The ACF cloth is installed downstream of a particle filter and air passing through the ACF cloth is supplied to the building interior. During periods of air cleaning, VOCs are removed from the air passing through the ACF cloth by adsorption on the ACF cloth. Periodically, e.g., each night, the adsorbed VOCs are removed from the ACF cloth by passing heated or unheated outdoor air through the cloth. The desorbed VOCs are vented to outdoors.

The present invention also provides for a device that cleans air or gas using one or more three air cleaning technologies, such as in an integrated manner to remove particles, volatile organic compounds (VOCs), and/or ozone from air. In some embodiments of the invention, the air or gas is indoor air or air from the outside of a building. In some embodiments of the invention, the air or gas is air or gas in need of removal and/or inactivation of particles, volatile organic compounds (VOCs), and/or ozone, such air or gas could be polluted or suspected of being polluted. One of the air cleaning technologies is the manganese-oxide-catalyst coated particle filter. Another of the air cleaning technology is the activated carbon fiber (ACF) filter.

The device comprises a chamber comprising an inlet and an outlet, and a manganese-oxide-catalyst coated particle filter and/or an activated carbon fiber (ACF) filter disposed inside the chamber between the inlet and outlet. Air or gas from outside the chamber enters the chamber and passes through the manganese-oxide-catalyst coated particle filter and/or an activated carbon fiber (ACF) filter and exits the chamber through the outlet, such that the manganese-oxide-catalyst coated particle filter removes particles, formaldehyde and/or other VOCs and the ACF filter removes volatile organic compounds (VOCs), and/or ozone from air or gas.

Figure 5:
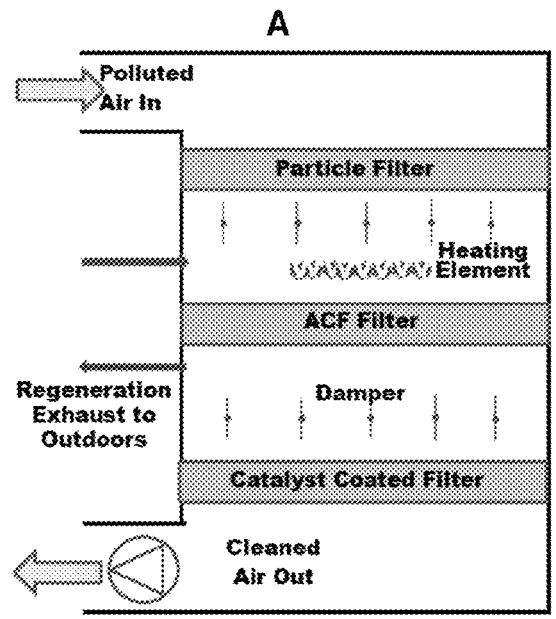
FIG. 5 shows (A) a device of the present invention, and (B) an activated carbon fiber system, a with optional heat exchanger, that can reduce the already low regeneration energy consumption (5 W time average for a 100 cfm system) by transferring heat from the hot exhaust regeneration air to the incoming outdoor regeneration air.
Figure 5:
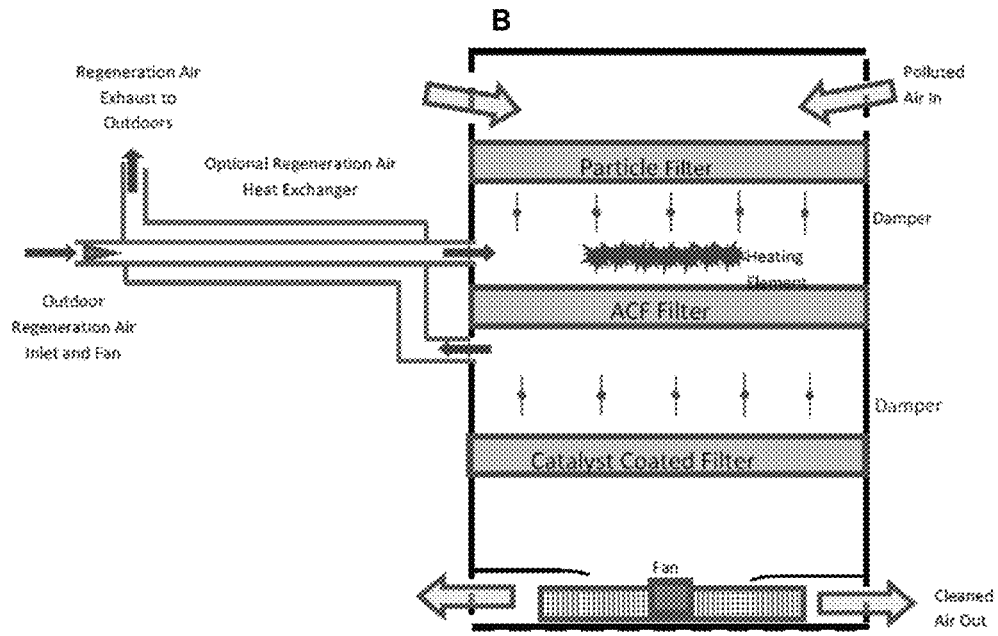

FIG. 5 shows one embodiment of the device. The air or gas, such as indoor air or air from the inside of a building, air enters from the top of the air cleaner and first passes through a particle filter that removes particles. The particle filter could be any of various existing types. In some embodiments of the invention, the particle filter comprises a pleated fibrous filter with a particle removal efficiency of 70% for 0.3 micrometer particles, and a higher efficiency for smaller and larger particles. The particle filter is capable of cleaning the air of particles and also protects the downstream filter elements in the air cleaner, extending their life. After passing through the particle filter, the air or gas then passes through an activated carbon fiber (ACF) filter that is capable of removing a broad spectrum of indoor VOCs. The ACF filter is capable of removing most VOCs identified as important in indoor air with an efficiency equal to or greater than about 10%, 20%, 50% or 70%. The ACF filter is also capable of removing ozone. In some embodiments of the invention, the air next passes through a catalyst-coated fibrous particle filter which is capable of removing formaldehyde with an efficiency equal to or greater than about 10%, 20%, 50% or 70%. The catalyst is the manganese oxide compound of the present invention in the form of a powder, with a nano-scale substructure, that is deposited on the fibers of the filter. The upstream ACF filter protects the catalyst from high molecular weight VOCs and consequently reduces the risk or speed of catalyst deactivation. In some embodiments of the invention, the air velocity in the air cleaner is maintained low, such as from one tenth to one half of a meter per second. Such low air velocities allow high pollutant removal efficiencies with low pressure drops, minimize fan energy requirements, and minimize noise associated with high velocity air movement. In some embodiments of the invention, the catalyst is applied to the ACF filter eliminating the need for a separate particle filter coated with the catalyst.

In some embodiments of the invention, the ACF filter element of the air cleaner removes VOCs from air by physical adsorption, which is a reversible process. The ACF filter can be periodically regenerated using heated outdoor air. The regeneration process drives previously adsorbed VOCs off the ACF filter and vents these VOCs to outdoors, preparing the ACF to again remove VOCs from indoor air. The regeneration period can be about 15 minutes per each 12 hour period of air cleaning. Such a regeneration period is sufficient if the regeneration air is heated to 150° C. The regeneration air flow rate needs to be only a few percent of the flow rate of cleaned air, thus, the energy required for heating the regeneration air is minimal. To implement the regeneration cycle, the main fan is turned off, the dampers above and below the ACF filter are closed, the regeneration fan is turned on, and the regeneration heater is turned on. VOCs are driven off the ACF and vented outdoors for about 15 minutes after which the system returns to normal operation. FIG. 5 shows an optional heat exchanger that can reduce the already low regeneration energy consumption by transferring heat from the hot exhaust regeneration air to the incoming outdoor regeneration air. The heat exchanger can be incorporated in the case of the air cleaner. Given the small regeneration air flow rates, only small tubes are needed for the regeneration air flow. In some embodiments of the invention, the device can further comprise a small particle filter and shut off valves required in the regeneration airflow path. In some embodiments of the invention, the air used for regeneration is outdoor air. In some embodiments of the invention, the air used for regeneration is indoor air.

In some embodiments of the invention, the device can be a version of the air cleaner that can be used in homes. FIG. 5 shows a unit for a residential application that draws polluted air from a room and exhausts cleaned air to the room; however, the inlet and/or outlet airstreams can also be ducted and connected to an air distribution system such as the duct system of a forced air furnace.

In some embodiments of the invention, the device is similar to that in FIG. 5 and is capable of processing a larger volume of air and with ducts for connection to commercial building heating, ventilation, and/or air conditioning systems.

FIG. 6 shows another embodiment of the device with an ACF filter with dampers and regeneration airflow hardware installed inside a heating ventilation, and air conditioning system. The particle filter shown in FIG. 6 may be, in some embodiments be coated with the catalyst or the ACF filter may be coated with catalyst, or the system may use only an ACF filter and no catalyst.

Benefits of the Present Invention

The device of the present invention, such as the air cleaner, can be used to improve indoor air quality by reducing indoor concentrations of particles, VOCs, and ozone. In some applications, indoor air quality may be improved to protect health without simultaneous reductions in ventilation (outdoor air supply).

In many buildings, the air cleaner can also enable large, such as about 50%, reductions in ventilation (i.e., outdoor air supply) to decrease heating and cooling energy. The air cleaner can more than compensate for the diminished removal of indoor-generated particles and VOCs by ventilation, thus, the system can enable ventilation rates to be reduced with simultaneous reductions in indoor particles and VOCs. Indoor ozone levels (ozone comes from outdoors) can also be diminished. Ventilation rate reductions will be possible in buildings without unvented combustion appliances, tobacco smoking, or strong sources of radon. Unvented combustion appliances and tobacco can be strong sources of inorganic gaseous pollutants, such as carbon monoxide, that are not removed by the air cleaner. In addition, radon, which normally comes from the soil around a building's foundation, may also not be significantly removed by the air cleaner, although further tests may demonstrate radon removal by the ACF filter. Given these criteria, ventilation rate reductions should be possible in a large majority of commercial buildings and in many homes. The air cleaner can provide a unit, with fewer particles and less VOCs than outdoor air, while consuming 15% to 20% of the energy of ventilation.

REFERENCES CITED

Ahmed, K. A. M., Q. M. Zeng, K. B. Wu and K. X. Huang (2010). "Mn3O4 nanoplates and nanoparticles: Synthesis, characterization, electrochemical and catalytic properties." *Journal of Solid State Chemistry* 183(3): 744-751.

Attenburrow, J., Cameron, A. F. B., Chapman, J. H., Evans, R. M., Hems, B. A., Jansen, A. B. A. and Walker, T., (1952)"A synthesis of vitamin A from cyclohexanone", *Journal of Chemical Society,* 1094-1111.

Baltanas, M. A., A. B. Stiles and J. R. Katzer (1986). "DEVELOPMENT OF SUPPORTED MANGANESE OXIDES FOR PARTIAL OXIDATION—COOXIDATION AND OXYGEN AVAILABILITY." *Applied Catalysis* 20(1-2): 15-29.

Benne, K., B. Griffith and e. al (2009). "Assessment of the energy impacts of outside air in the commercial sector." *NREL/TP*-550-41955. Golden, Colo., National Renewable Energy Laboratory.

Blish, D. and Post, E., (1989), "Thermal behavior of complex, tunnel-structure manganese oxides", *American Mineralogist,* 74, 177-186, Brooks, C. S. (1965). "REACTION OF HYDROGEN WITH A NONSTOICHIOMETRIC MANGANESE DIOXIDE." *Journal of Catalysis* 4(5): 535-&.

Brooks, C. S. (1967). "KINETICS OF HYDROGEN AND CARBON MONOXIDE OXIDATION OVER A MANGANESE OXIDE." *Journal of Catalysis* 8(3): 272-&.

Cellier, C., V. Ruaux, C. Lahousse, P. Grange and E. M. Gaigneaux (2006). "Extent of the participation of lattice oxygen from gamma-MnO2 in VOCs total oxidation: Influence of the VOCs nature." *Catalysis Today* 117(1-3): 350-355.

Chen, H. M., J. H. He, C. B. Zhang and H. He (2007). "Self-assembly of novel mesoporous manganese oxide nanostructures and their application in oxidative decomposition of formaldehyde." *Journal of Physical Chemistry C* 111(49): 18033-18038.

Chen, T., H. Y. Dou, X. L. Li, X. F. Tang, J. H. Li and J. M. Hao (2009). "Tunnel structure effect of manganese oxides in complete oxidation of formaldehyde." *Microporous and Mesoporous Materials* 122(1-3): 270-274.

Ciminov, A, Indovian, V. Catalytic activity of Mn3+ and Mn4+ ions dispersed in MgO for CO oxidation, J. Catal 33 (1974) 493

Cogliano, V. J., Y. Grosse, R. A. Baan, K. Straif, M. B. Secretan and F. El Ghissassi (2005). "Meeting report: summary of IARC monographs on formaldehyde, 2-butoxyethanol and 1-tert-butoxy-2-propanol." *Environ. Health Perspectives* 113: 1205-1208.

Destaillats, H., M. M. Lunden, B. C. Singer, B. K. Coleman, A. T. Hodgson, C. J. Weschler and W. W. Nazaroff (2006). "Indoor secondary pollutants from household product emissions in the presence of ozone. A bench scale study." *Environ. Sci. Technol.* 40: 4421-4428.

Doornkamp, C. and V. Ponec (2000). "The universal character of the Mars and Van Krevelen mechanism." *Journal of Molecular Catalysis a-Chemical* 162(1-2): 19-32.

Girman, J. R., S. E. Womble and E. L. Ronca (1995). "Developing baseline information on buildings and indoor air quality (BASE 94): Part II—Environmental pollutant measurements and occupant perceptions." *Proceedings of Healthy Buildings* 95, 3: 1311-1316.

Griffith, B., N. Long and e. al (2008). "Methodology for modeling building energy performance across the commercial sector." *NREL/TP-550-41956. Golden, Co. National Renewable Energy Laboratory.*

Harfenist, M., Bayley, A., and Lazier, W. A., (1954), "The oxidation of allyl and benzyl alcohols to the aldehydes", *Journal of Organic Chemistry*, 19, 1608-1616

Hodgson, A. T., D. Beal and J. E. R. McIlyaine (2002). "Sources of formaldehyde, other aldehydes and terpenes in a new manufactured house." *Indoor Air* 12: 235-242.

Hodgson, A. T. and H. Levin (2003). Volatile organic compounds in indoor air: a review of concentrations measured in North America since 1990. Berkeley, Calif., Lawrence Berkeley National Laboratory: LBNL Report 51715.

Kobayashi. M and Kobayashi. H (1972). "Application of transient-response method to study of heterogeneous catalysis. 1. Nature of catalytically active oxygen on manganese-dioxide for oxidation of carbon-monoxide at low-temperatures." *Journal of Catalysis* 27(1): 100-&.

Kobayashi, M, Matsumoto, H. and Kobayashi H (1971). "Distribution of oxidation power of surface oxygen species on manganese dioxide during oxidation of carbon monoxide." *Journal of Catalysis* 21(1): 48-&.

Maddalena, R., M. Russell, D. P. Sullivan and M. G. Apte (2009). "Formaldehyde and Other Volatile Organic Chemical Emissions in Four FEMA Temporary Housing Units." *Environmental Science & Technology* 43(15): 5626-5632.

Mendell, M. J. (2007). "Indoor residential chemical emission as risk factors for respiratory and allergic effects in children: a review." *Indoor Air* 17: 259-277.

NIOSH, (1992) NIOSH recommendations for occupational safety and health. Compendium of policy documents and statements. DHHS (NIOSH) Publication No. 92-100. http://www.cdc.gov/niosh/pdfs/92-100-c.pdf, National Institute for Occupational Safety and Health Prasad, V. S. and M. Chaudhuri (1995). "removal of bacteria and turbidity from water by chemically treated manganese and iron-ores." *Journal of Water Supply Research and Technology-Aqua* 44(2): 80-82.

Post, J. E. (1999). "Manganese oxide minerals: Crystal structures and economic and environmental significance." *Proceedings of the National Academy of Sciences of the United States of America* 96(7): 3447-3454.

Sekine, Y. (2002). "Oxidative decomposition of formaldehyde by metal oxides at room temperature." *Atmospheric Environment* 36(35): 5543-5547.

Sekine, Y. and A. Nishimura (2001). "Removal of formaldehyde from indoor air by passive type air-cleaning materials." *Atmospheric Environment* 35(11): 2001-2007.

Singer, B. C., H. Destaillats, A. T. Hodgson and W. W. Nazaroff (2006). "Cleaning products and air fresheners: emissions and resulting concentrations of glycol ethers and terpenoids." *Indoor Air* 16: 179-191.

Tang, X. F., J. L. Chen, X. M. Huang, Y. Xu and W. J. Shen (2008). "Pt/MnOx-CeO2 catalysts for the complete oxidation of formaldehyde at ambient temperature." *Applied Catalysis B-Environmental* 81(1-2): 115-121.

Tang, X. F., J. H. Li and J. M. Hao (2010). "Significant enhancement of catalytic activities of manganese oxide octahedral molecular sieve by marginal amount of doping vanadium." *Catalysis Communications* 11(10): 871-875.

Tang, X. F., Y. G. Li, X. M. Huang, Y. D. Xu, H. Q. Zhu, J. G. Wang and W. J. Shen (2006). "MnOx-CeO2 mixed oxide catalysts for complete oxidation of formaldehyde: Effect of preparation method and calcination temperature." *Applied Catalysis B-Environmental* 62(3-4): 265-273.

USEPA (2003). A standardized EPA protocol for characterizing indoor air quality in large office buildings. Washington D.C.

Wen, Y. R., X. Tang, J. H. Li, J. M. Hao, L. S. Wei and X. F. Tang (2009). "Impact of synthesis method on catalytic performance of MnOx-SnO2 for controlling formaldehyde emission." *Catalysis Communications* 10(8): 1157-1160.

Xu, Q., Y. Zhang, J. Mo, R. Ke and S. Kang (2008). "Research of formaldehyde removal by room temperature thermo-catalytic oxidation reactor." *Proceedings of Indoor Air* 2008 Paper ID 692, Copenhagen, Denmark.

Yuan, J. K.; Li, W. N.; Gomez, S.; Suib, S. L., Shape-Controlled Synthesis of Manganese Oxide Octahedral Molecular Sieve Three-Dimensional Nanostructures, J. Am. Chem. Soc. 2005, 127, 14184.

Yuan, J.; Laubernds, K.; Zhang, Q.; Suib, S. L., Self-Assembly of Microporous Manganese Oxide Octahedral Molecular Sieve Hexagonal Flakes into Mesoporous Hollow Nanospheres, J. Am. Chem. Soc. 2003, 125, 4966

Zwicker W K, Meijer W O J G, Jaffe H W, (1962), "Nsutite a widespread manganese oxide mineral", *American Mineralogist* 47, 246-266.

Zhong, L.; Hu, J.; Liang, H.; Cao, A.; Song, W.; Wan, L. Self-Assembled 3D Flowerlike Iron Oxide Nanostructures and Their Application in Water Treatment, AdV. Mater. 2006, 18, 2426.

Each cited reference is herein incorporated by reference.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

In this study, we synthesized novel $MnO_x$ catalysts ($1<x<2$), and evaluated experimentally the efficacy of filters coated with this material to oxidize formaldehyde with moderately low pressure drops. The results obtained in this study illustrate the potential of this approach as an effective indoor formaldehyde removal technology.

Experimental Methods

Preparation of Manganese Oxide Catalysts.

Sodium permanganate ($\geq 97\%$) and manganese sulfate monohydrate ($\geq 98\%$) were obtained from Sigma Aldrich and used without further purification. Manganese dioxide ($>98\%$) was also obtained from Sigma Aldrich to use as a reference in formaldehyde removal tests. Manganese oxide samples were prepared using a chemical co-precipitation route. Manganese sulfate ($MnSO_4$) and sodium permanganate ($NaMnO_4$) are dissolved in distilled water. To the manganese sulfate aqueous solution, the sodium permanganate solution was added slowly with constant stirring such that the molar ratio of the resulting solution of sodium permanganate to manganese sulfate was maintained at a ratio 2:3, leading to precipitation of an oxide. The resulting black suspension was kept at room temperature for 24 hours. The suspension was then filtered, and the precipitate was washed with deionized water several times to remove any impurities. Three different aliquots of the precipitate were heated in air for 12 hours at 100, 200 and 400° C., respectively, to prepare three different catalyst materials.

Catalyst Characterization Techniques

BET Surface Area Analysis.

Brunner Emmet and Teller (BET) surface area was obtained using a Porosimeter analyzer (Micromeritics 3000). Nitrogen was used as the sorption gas to study the BET isotherm and obtain surface area and pore volume. About 1 g of each sample was previously degassed for a period of 12 hours under a stream of nitrogen at 100° C.

X-Ray Diffraction.

The material was ground under hexane, and a few drops of the slurry were applied onto a silicon zero background plate (ZBP) placed on a warm hotplate. When dry, the ZBP was placed in a holder and examined using a Panalytical X'Pert diffractometer. Raw x-ray diffraction data were merged (12, 2 hour scans), an empirical background was removed, the K alpha 2 contribution was stripped, and the scans were smoothed using a Fourier filter. Peaks were selected using the peak picking utility, and phases were determined using a library search by matching utility with all manganese files in the database. Crystallite size was obtained using the Scherrer equation.

SEM Imaging Analysis.

SEM imaging was performed using a Hitachi SE4000 Scanning electron microscope. Samples were mounted on a specimen mount and sputter coated with gold nano-particles before analysis.

ICP MS Analysis.

Manganese oxide samples were analyzed using a Perkin Elmer DRCII Inductively Coupled Plasma-Mass Spectrometer (ICP-MS). To measure the concentrations of Mg, K, Ca, Cr and Fe, the instrument was used in DRC (Dynamic Reaction Cell) mode using ammonia as reaction gas to remove interferences. Other elements were analyzed in standard mode. Gallium was used as an internal standard.

Evaluation of Formaldehyde Elimination

Preparation of Supported Catalysts.

Formaldehyde removal was studied using a continuous flow system. The catalyst support used in this study was a heating ventilation and air conditioning (HVAC) particle filter. Manganese oxide is synthesized using pre-designated precipitation procedure. The manganese oxide is ground to fine powder with size range<3 µm using a mortar and pestle and placed in the canister of a powder-based spray system. The system uses pressurized air (about 30 psi) to aerosolize and dispense the powder. Initially, the uncoated filter material is weighed. It is then positioned in the filter coating mount as shown in FIG. 7. This mount consists of the filter being placed in an enclosure fitted with a series of HEPA filters downstream of the filter that is to be coated with manganese oxide. A fan is fitted in the back end of the HEPA filters to pull air through when coating is taking place. After the coating process is complete the filter is turned in the opposite direction and dry air is blown through to remove excess manganese oxide. To ensure that any remaining lose particles of manganese oxide are removed the filter is shaken vigorously. The coated filter is then weighed in order to determine the weight of manganese oxide that is loaded on the filter surface. The filter was then removed from the open faced filter holder and transferred into a 47-mm custom made alumina filter holder. The procedure was repeated for commercially obtained manganese oxide to compare the performance efficiency between the laboratory prepared and commercially available manganese oxide samples.

Experimental Setup.

Formaldehyde-enriched indoor air was generated using two different experimental setups. In one case, we used as a formaldehyde source seven 4×4 inch highly emitting specimens of cabinetry obtained in a recent study (Maddalena et al. 2009). These stable diffusive sources were placed inside a 200-L bench chamber, obtaining formaldehyde concentrations in the range 150-200 ppb. The other setup consisted on a 20-$m^3$ chamber ventilated at an air exchange rate of 1 $h^{-1}$, in which lower levels of formaldehyde (30-40 ppb) were achieved by continuously infusing an aqueous solution of the target compound using a syringe pump. Two experiments at different face velocities were conducted using each of the experimental setups, to evaluate the efficiency of the catalyst at high and low air flows. Air from each of the chambers was pulled through the filter holder containing the supported manganese oxide catalyst at the rate of 0.1 L $min^{-1}$ (bench chamber) and 30 L $min^{-1}$ (large chamber). These corresponded to a face velocity of 0.002 m $s^{-1}$ and 0.5 m $s^{-1}$, respectively. Aldehyde samples were collected simultaneously upstream and downstream of the filter holder in all cases.

Sampling and Analytical Methods.

Integrated volatile carbonyl samples were collected upstream and downstream of the catalyst using dinitrophenyl hydrazine (DNPH)-coated silica samplers (Waters) at a rate of 20 $cm^3$ $min^{-1}$ using peristaltic pumps. Ambient ozone was removed with potassium iodide scrubbers preceding each DNPH sampler (Waters Sep-pak Ozone scrubber). The concentration value reported in each case corresponds to a time-integrated average over the sampled period, and is reported at the center of each sampling period. The flow corresponding to each sample was measured using a primary air flow calibrator (Gilibrator®) with a precision greater than 2%. DNPH cartridges were extracted with 2-mL aliquots of acetonitrile, and the extracts were analyzed by HPLC with UV detection ($\lambda_{max}$=360 nm). A calibration curve for quantification was carried out using authentic standards of the DNPH hydrazone.

Evaluation of the Extent of Mineralization.

Carbon dioxide levels produced as a final byproduct of formaldehyde mineralization were estimated in separate tests using a mid-IR Picaro iCO$_2$ analyzer, CBDS 07. Ultra-high purity nitrogen and oxygen (99.999% pure) (Alliance Gas) with minimal CO$_2$ background levels (<1 ppb) were used for this evaluation. A gas stream was connected to a formaldehyde source consisting on 20 ml of a 37% aqueous formaldehyde solution in a 100 ml beaker, placed inside a 4-L stainless steel flow cell. The net flow of gas mixture through the flow cell was maintained at 8 L min$^{-1}$ and the nitrogen to oxygen ratio was 7:3. The upstream and downstream gas samples were collected in two 5-L Mylar bags for off-line CO$_2$ analysis. Formaldehyde present in upstream and downstream samples was stripped using DNPH-coated silica cartridges (Waters Sep-pak) to avoid spectral interference with the iCO$_2$ analyzer. These cartridges were subsequently extracted with acetonitrile solution for aldehyde analysis. In order to analyze the possibility of partial oxidation by-products, tests were also conducted to identify the formation of formic acid. Upstream and downstream formic acid gas samples were collected in a 0.01 N sodium hydroxide solution using glass impingers, and analyzed by Ion Chromatography (Dionex ICS 2000). Standards were prepared using 1 g/L sodium formate solution (Sigma Aldrich, Formate standard for IC) to identify and quantify formic acid, if present.

Results and Discussion

Catalyst Characterization

BET Surface Area Analysis.

BET surface area measurements obtained for the different materials tested in this study are listed in

TABLE 1

Table 1. BET surface area of different manganese oxides.

| Sample | Curing temperature (° C.) | BET Surface area (m$^2$ g$^{-1}$) |
|---|---|---|
| LBNL-100 | 100 | 149 |
| LBNL-200 | 200 | 103 |
| LBNL-400 | 400 | 93 |
| Commercial MnO$_2$ | — | 4 |

It should be noted that the BET surface area of commercial manganese oxide is much lower than the BET surface area of the manganese oxide prepared in the lab. Further, it was also observed that the BET surface area of the manganese oxide was inversely proportional to the temperature of curing.

X-Ray Diffraction Analysis.

Results of X-Ray diffraction for the different preparations of manganese oxide are shown in FIG. 1 (A)-(C). Table 2 shows the crystallite composition of the bulk phase of the manganese oxide samples. For samples LBNL-100 and LBNL-200, the X-ray diffraction spectra show combinations of intense and low reflections characteristic of the nsutite and cryptomelane phases of manganese oxide. Cryptomelane was the best match for samples LBNL-100 and LBNL-200 but did not match all lines. Nsutite was found to best correspond the unmatched lines with the best agreement on intensities. The sample treated at 400° C. was well reproduced by the pyrolusite signatures. X-ray diffraction spectra of manganese oxide sample obtained after reaction with formaldehyde was also obtained. The sample reacted continuously over a 42-day period, with a total formaldehyde conversion of 9.2 μg per m$^2$ of catalyst surface. It was found that although the sample maintained the same crystal structure property as that of the unreacted manganese oxide, the X-ray diffraction signatures of nsutite and cryptomelane shifted, showing a reduction in bulk phase of the catalyst causing an increase in the crystal spacing (d=2.42 A). The crystallite sizes were observed to be from 59 A to 101 A.

TABLE 2

Composition of manganese oxide prepared in the laboratory

| Material ID | Compound Name | Chemical Formula | Crystallite Size |
|---|---|---|---|
| LBNL-100 | Nsutite | Mn$^{4+}_{1-x}$Mn$^{2+}_x$O$_{2-2x}$(OH)$_{2x}$ where x = 0.06-0.07, corresponding to a mixture of 12.20% MnO/84.71% MnO$_2$ | 40-64 |
| LBNL-200 | Cryptomelane Nsutite | KMn$^{4+}_6$Mn$^{2+}_2$O$_{16}$ Mn$^{4+}_{1-x}$Mn$^{2+}_x$O$_{2-2x}$(OH)$_{2x}$ where x = 0.06-0.07, corresponding to a mixture of 12.20% MnO/84.71% MnO$_2$ | 66-101 |
| LBNL-400 | Cryptomelane Pyrolusite Cryptomelane-Q | KMn$^{4+}_6$Mn$^{2+}_2$O$_{16}$ MnO$_2$ KMn$^{4+}_6$Mn$^{2+}_2$O$_{16}$ | 84-101 |

The results of the X-Ray diffraction spectrum show that phase change occurs, leading to larger crystallite size as curing temperature increased. The X-ray spectrum of reacted manganese oxide species show no phase change and hence no significant oxidation state change, further supporting the hypothesis that manganese oxide acts as a catalyst and does not undergo any permanent change with the oxidation reaction of the surface reacting species.

SEM Surface Analysis.

Figure 2:
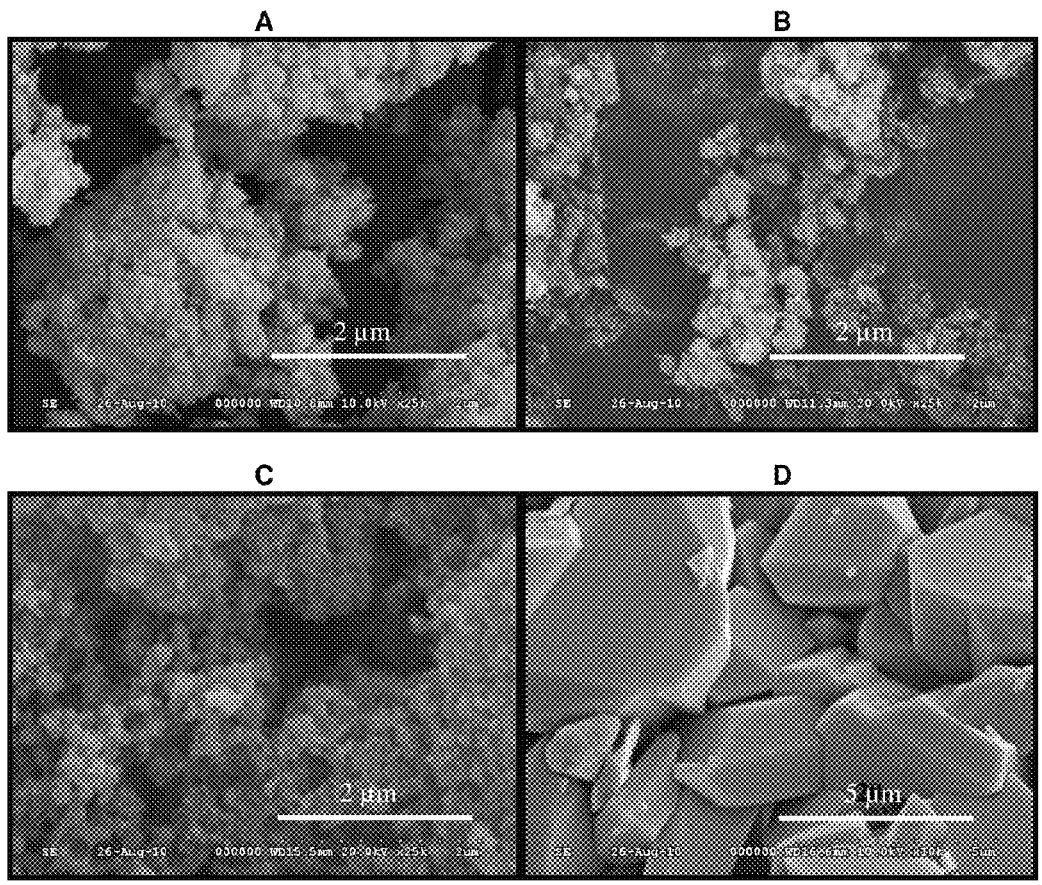
FIG. 2 shows SEM Images of manganese oxide particles synthesized and treated at (A) 100° C.; (B) 200° C.; (C) 400° C.; and (D) commercially available $MnO_2$.

FIGS. 2 (A), (B), and (C) show the scanning electron microscopy (SEM) images of manganese oxide samples LBNL-100, LBNL-200 and LBNL-400 respectively. FIG. 2 (D) shows the SEM image of commercially available MnO$_2$ (Sigma Aldrich). It was found that the manganese oxide samples synthesized in the lab were highly porous and had monodisperse nanospherical particles with diameter smaller than 50 nm. The commercially available manganese oxide was found to be crystalline and had particles with well defined crystal shape and size greater than 2 μm. It can be seen from SEM images of the laboratory synthesized manganese oxide that each nanospherical particle consisted of platelets that were aligned perpendicular to the spherical surface which is very similar to a honeycomb structure. This structural formulation is due to the hydrothermal precipitation method of synthesis of these materials (Yuan et al., 2005, Yuan et al., 2003, Zhong et al., 2004).

Determination of Empirical Formulae.

The results from ICP-MS analysis are shown in Table 3, and are in accordance with those from X-ray diffraction studies. We identified minor constituents such as sodium and potassium, as well as other impurities such as iron, and other metals, present in trace quantities. The empirical formula, mineral allotropic form and the oxidation state of manganese in the samples were determined using the ICP-MS data. The manganese oxide synthesized from the precipitation method used in this study hosts water molecules in the void spaces of the crystal structure under ambient conditions. The SEM results show the honeycomb structure of the synthesized manganese oxide suggesting the presence of voids that can incorporate water molecules in interstitial spaces. Previous studies (Blish and Post, 1989) on the thermal evolution of water reported the presence of water in the porous structures of manganese oxide. Further, they have observed that with increasing the temperature of curing of manganese oxide, the water content decreased, and was reduced drastically at 500° C. Additionally at higher temperature, oxygen evolution also takes places, leading to structural effects and phase change (Blish and Post, 1989). Post (1999) and Zwicker et al. (1962) suggested that the nsutite structure of manganese oxide has large channels leading to water uptake (in the order of ~10% by mass) facilitated by cations such as sodium, calcium, iron and magnesium present in such spaces. The empirical formulae for the different laboratory synthesized manganese oxide were calculated from the ICP-MS results by assuming the presence of water in the interstitial voids. Further, the allotropic forms of manganese oxide as observed from the X-Ray diffraction results have been used as the basis to estimate the percentage of each phase present in these samples. The mass fraction of manganese present suggests that $Mn^{2+}$ and $Mn^{4+}$ are the most predominant oxidation state of the synthesized material. The dual oxidation states present in samples LBNL-100 and LBNL-200 explain the active form of these minerals leading to the room temperature oxidation of formaldehyde (Attenburrow et al., 1952; Harfenist et al., 1954). The pores of pyrolusite (the predominant form in samples treated at 400° C.) are smaller, and hence cannot accommodate higher moisture unlike nsutite (predominantly present in samples LBNL-100 and LBNL-200) further supporting this hypothesis.

TABLE 3

Elemental analysis of $MnO_x$ samples using ICP-MS

| Sample | $MnO_x:H_2O$ ratio (mass %) | Element | Mass fraction present in the sample | $MnO_x$ phase and empirical formula |
|---|---|---|---|---|
| LBNL-100 | 85:15 | Mn | 63.1 | 94% nsutite |
| | | Na | 0.35 | $(Mn^{4+}_{0.85}O_{1.7}Mn^{2+}_{0.15}(OH)_{0.3})$, |
| | | K | 0.29 | 5.3% cryptomelane |
| | | Fe | 0.03 | $(KMn^{4+}_6Mn^{2+}_2O_{16})$ |
| LBNL-200 | 84:16 | Mn | 63.0 | 95% nsutite |
| | | Na | 0.37 | $(Mn^{4+}_{0.85}O_{1.7}Mn^{2+}_{0.15}(OH)_{0.3})$, |
| | | K | 0.26 | 4.9% cryptomelane |
| | | Fe | 0.04 | $(KMn^{4+}_6Mn^{2+}_2O_{16})$ |
| LBNL-400 | 91:9 | Mn | 63.1 | 100% pyrolusite $(Mn^{4+}O_2)$ |
| | | Na | 0.34 | |
| | | K | 0.23 | |
| | | Fe | 0.04 | |

Formaldehyde Elimination Studies.

Formaldehyde removal (if) was calculated with equation 3 where $[F]_{up}$ is the upstream formaldehyde concentration and $[F]_{dn}$ is the downstream formaldehyde concentration (both expressed in μg m$^{-3}$), $$\eta_f = \left( \frac{[F]_{up} - [F]_{dn}}{[F]_{up}} \right) \times 100 \quad (3)$$

Figure 3:
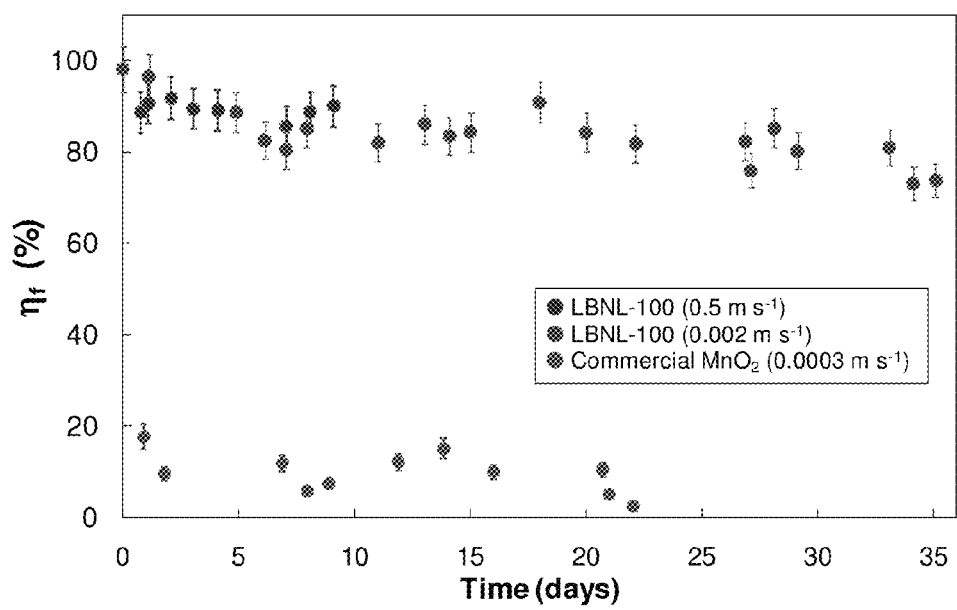
FIG. 3 shows formaldehyde removal if vs. time.

FIG. 3 shows the performance of LBNL manganese oxide to remove formaldehyde at two different face velocity conditions, together with data corresponding to commercially available manganese oxide. For the low face velocity conditions (0.002 m s$^{-1}$), the formaldehyde levels upstream were maintained at 150-200 ppb, while for high face velocity (0.5 m s$^{-1}$) the formaldehyde concentration was maintained at 30-45 ppb. The mass of laboratory manganese oxide sample loaded on the support was 110 mg and the mass of the commercial manganese oxide sample was 320 mg. The laboratory-synthesized manganese oxide performed significantly better than commercial $MnO_2$. Formaldehyde removal results obtained for laboratory synthesized manganese oxide for the higher face velocity (0.5 m s$^{-1}$) were similar to those observed in for lower face velocity. One other major difference other than the face velocity in these experiments was the formaldehyde concentration. The levels of formaldehyde for the experiments at high face velocity were maintained between 30-40 ppb, which is ~5 times lower than the experiments shown in FIG. 3 for the low face velocity tests, and closer to the levels found in buildings. In order to text extreme worst-case scenario conditions, a separate short test was carried out for a period of 12 h with a high formaldehyde concentration of 150 ppb and the high face velocity of 0.5 m s$^{-1}$. Under these extreme conditions, the removal efficiency was higher than 60%.

Figure 4:
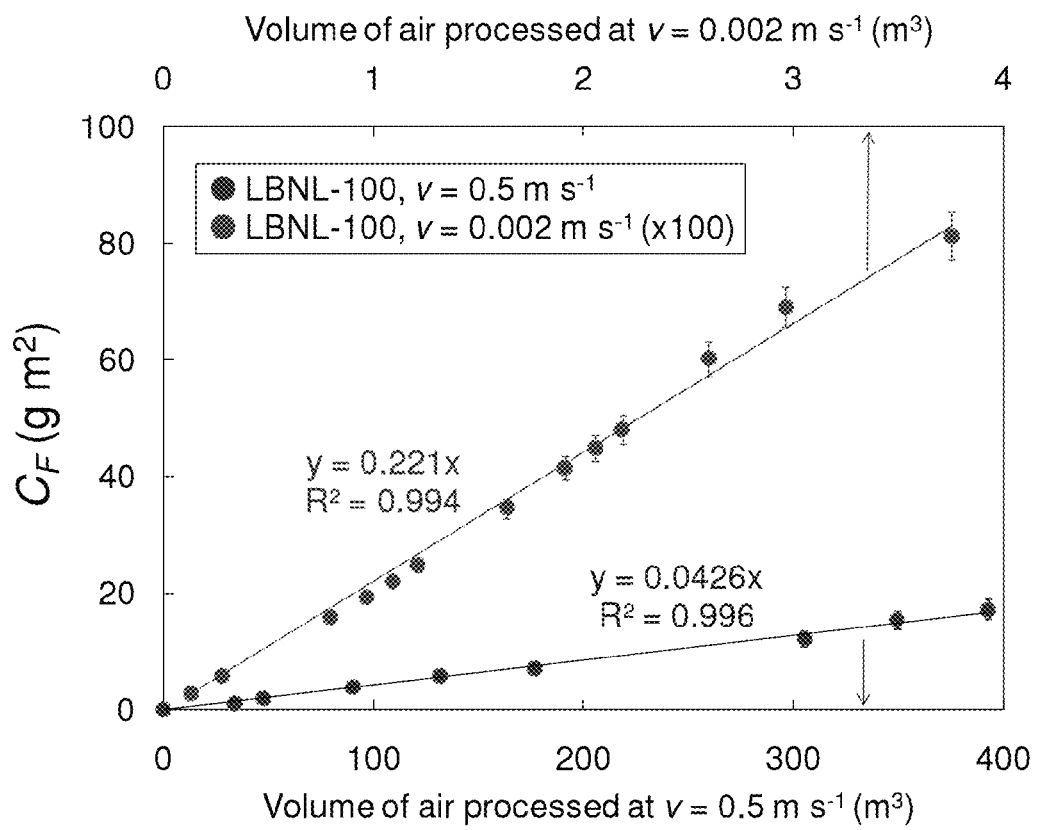
FIG. 4 shows cumulative formaldehyde mass reacted on manganese oxide catalyst as a function of volume of air processed.

FIG. 4 shows the cumulative mass of formaldehyde reacted per unit filter face area ($C_F$) at the two different face velocities as a function of the volume of air processed, defined as:

$$C_F = \frac{1}{S} \int_0^t f \cdot [F]_{up} \cdot dt \quad (4)$$

where S is the filter face area (in m$^2$) and f is the air flow (in m$^3$ min$^{-1}$). The cumulative formaldehyde mass removed increased linearly with time in both cases, because the removal efficiency was relatively constant during the studied periods. Since the volume of air processed at v=0.5 m s$^{-1}$ was ~100 times higher than the volume of air processed at v=0.002 m s$^{-1}$, the $C_F$ values in each case follows the same proportion. The difference in slopes shown in FIG. 4 can be attributed simply to the differences in upstream formaldehyde concentrations between both experiments, with ~5 times higher $[F]_{up}$ for the experiment carried out at v=0.002 m s$^{-1}$. These results suggest that the reaction was not limited by mass transfer effects in this range of face velocities.

Mineralization.

The oxidation of formaldehyde catalyzed by manganese oxide surfaces is expected to proceed through the MvK mechanism as stated in equations 1 and 2, leading ultimately to mineralization (i.e., formation of carbon dioxide and water). The concentration of carbon dioxide released due to the oxidation of formaldehyde was measured to evaluate the extent of mineralization under the current experimental conditions. The upstream and downstream formaldehyde and carbon dioxide concentrations recorded in two separate experiments are listed in Table 4. These tests were performed at higher formaldehyde concentrations than the experiments reported above (by factors between 15 and 200) due to the low sensitivity of the i$CO_2$ analyzer to ppb levels of carbon dioxide. Within the experimental error, the extent of mineralization was 100% in both experiments. These results suggest that formaldehyde undergoes complete mineralization in good agreement with the proposed MvK mechanism even at concentrations that are much higher than those typically found in buildings.

TABLE 4

Formaldehyde and Carbon-dioxide upstream and downstream concentrations

| Experiment Number | Compound | Upstream Concentration | Downstream Concentration | Concentration Difference |
|---|---|---|---|---|
| 1 | Formaldehyde | 6.06 ± 0.16 | 1.97 ± 0.05 | −4.09 ± 0.21 |
|  | Carbon dioxide | 0.04 ± 0.19 | 4.11 ± 0.18 | 4.07 ± 0.37 |
| 2 | Formaldehyde | 2.84 ± 0.09 | 0.88 ± 0.03 | −1.96 ± 0.12 |
|  | Carbon dioxide | 0.62 ± 0.30 | 2.54 ± 0.07 | 1.92 ± 0.37 |

Formic acid was not detected in downstream samples, further supporting the observation of a complete mineralization of formaldehyde.

CONCLUSIONS

A manganese oxide catalyst was synthesized using inexpensive precursors and a simple process. Relative to the commercial product, the synthesized manganese oxide has a much higher surface area and different crystal size and chemical composition, consistent with superior catalytic performance. The synthesized catalyst, adsorbed on a typical particle filter, removed formaldehyde with a stable ~80% efficiency at room temperature. Modeling indicated that deployment of this catalyst in the supply airstreams of HVAC systems would substantially reduce indoor formaldehyde concentrations even when ventilation rates are reduced by 50% to save energy.

Modeling results of Xu et al (2008) indicate that 20% formaldehyde removal efficiency could be obtained using a $MnO_2$-coated honeycomb media with very low pressure drop (about 2 to 3 Pa) with face velocities typical of air filter systems. Assuming typical ratios of outdoor air ventilation flow to total supply air flow in commercial heating ventilation and air conditioning (HVAC) systems, 15% to 20% formaldehyde removal efficiency in the supply airstream is adequate to counteract the expected indoor level increases associated with a 50% reduction in minimum outdoor air supply. Given that total supply airstream pressure drops are often 500-1000 Pa, the predictions of Xu et al 2008 suggest that the pressure drops and associated fan energy requirements of manganese oxide-coated honeycomb media air cleaning may be negligible.

Example 2

In some embodiments of the invention, the device comprises an integrated-technology air cleaner (ITAC) capable of removing VOCs, and optionally particles and optionally ozone, from indoor air with a high efficiency. The device has approximately the same rates of removal of indoor-generated particles and VOCs in a typical single-family house, and also reduces indoor concentrations of outdoor-air VOCs and ozone. In some embodiments of the invention, the device has an air flow rate of 100 cfm, a removal efficiency of 70% for a range of VOCs and for 0.3 micrometer size particles, and a time-average power consumption less than 50 w.

FIG. 5 shows a schematic of the design of the air cleaner which uses three air cleaning technologies in an integrated manner to remove particles, volatile organic compounds (VOCs), and ozone from indoor air. Indoor air enters from the top of the air cleaner and first passes through a particle filter that removes particles. The particle filter could be any of various existing types. We envision, for example, using a pleated fibrous filter with a particle removal efficiency of 70% for 0.3 micrometer particles, and a higher efficiency for smaller and larger particles. The particle filter cleans the air of particles and also protects the downstream filter elements in the air cleaner, extending their life. After passing through the particle filter, the air then passes through an activated carbon fiber (ACF) filter that removes a broad spectrum of indoor VOCs with approximately 70% efficiency, but with a 20% efficiency for formaldehyde. Based on our prior research showing that small amounts of activated carbon can remove ozone for an extended period, the ACF filter is also expected to remove ozone, although we have not yet quantified the removal efficiency. Next, the air passes through a fibrous particle filter coated with an LBNL-synthesized manganese oxide catalyst which, based on our tests, will remove formaldehyde with an efficiency of approximately 70%. The upstream ACF filter protects the catalyst from high molecular weight VOCs and consequently reduces the risk or speed of catalyst deactivation. Air velocities in the air cleaner are maintained low, a few tenths of a meter per second. These low air velocities allow high pollutant removal efficiencies with low pressure drops, minimize fan energy requirements, and minimize noise associated with high velocity air movement. The ACF filter is periodically regenerated using heated outdoor air to drive previously adsorbed VOCs off the ACF filter and vent these VOCs to outdoors, preparing the ACF to again remove VOCs from indoor air. To implement the regeneration cycle, the main fan is turned off, the dampers above and below the ACF filter are closed, the small regeneration fan is turned on, and the regeneration heater is turned on. VOCs are driven off the ACF and vented outdoors for approximately 15 minutes after which the system returns to normal operation. FIG. 5 shows an optional heat exchanger that can reduce the already low regeneration energy consumption (5 W time average for a 100 cfm system) by transferring heat from the hot exhaust regeneration air to the incoming outdoor regeneration air. In practice, the heat exchanger would be incorporated within the case of the air cleaner. With the small regeneration air flow rates, only small tubes are needed for the regeneration air flow. Not shown are the small particle filter and shut off or backflow prevention valves required in the regeneration airflow path. FIG. 5 shows a schematic of unit for a residential application that draws polluted air from a room and exhausts cleaned air to the room; however, the inlet and/or outlet airstreams can also be ducted and connected to an air distribution of a forced air furnace or a commercial HVAC system.

Based on component costs, we expect the ITAC to have an acceptable cost. The estimated consumer's cost is $20 for the particle filter in a residential-size ITAC. The cost of the ACF media used to construct the ACF filter is approximately $3-$4. With the low system velocities, only a single unpleated layer of ACF is needed. The filter pad used as the support for the catalyst will cost only a couple dollars. We don't yet have a cost for the catalyst, but note that the amount of catalyst is small, no rare or expensive materials are used, the catalyst synthesis is simple, and that we have a simple process using off-the-shelf hardware for depositing the catalyst on the filter pad. All of the filtration elements will need to be replaced occasionally. With the low system velocities, we anticipate at least a one-year life for the particle filter. Further tests are needed to quantify the life of the ACF and catalyst, but a multiyear life seems feasible. The remaining ITAC hardware is relatively simple, with the fan and dampers being the most expensive.

In one example of a unit with 100 cfm Primary Air Flow, the air cleaner can have the following the properties: Filter face areas=1.7 ft$^2$ (0.16 m$^2$), face velocities=60 fpm (0.3 m/s), Minimum particle removal efficiency=70% at 0.3 microns, ACF Filter Efficiency for VOCs=70% (except 20%-25% for formaldehyde), Catalyst Coated Filter Efficiency for Formaldehyde=70%, Regeneration air flow=3 cfm, for 30 minutes per day, approx. 1 inch dia. regeneration air tubing, Regeneration heater power 250 W, or 125 W with heat exchanger, Regeneration air temperature=300° F. (150° C.), Regeneration heater equivalent steady state power=5 W (or 2.5 W with heat exchanger), Total pressure drop for primary airflow=approx. 0.4 IWG (100 Pa), and Primary fan power=approximately 40 to 60 W. The Operational Sequence of the unit may be the following: for 11.45 hr of each 12 hr, primary fan operates, dampers remain open and air is cleaned; and, for 15 minutes of each 12 hours, regeneration fan and heater operate and dampers are closed and ACF filter is regenerated. The unit can further comprise one or more of the following: shut-off valves and particle filter in regeneration air tubing, the primary air inlet or outlet may be duct connected, and/or regeneration air heat exchanger.

Example 3

Manganese Oxide Catalysts

In a field demonstration, deployment of a catalyst-treated filter reduces indoor formaldehyde concentrations by about 80%. Tests indicated that high humidity conditions do not significantly affect the performance of the manganese oxide catalysts. Test indicate little inactivation of the catalyst after long-term continuous use.

ACF Systems.

Heating air to regenerate the ACF media results in improved regeneration efficiency with respect to that achieved by directly heating the media, a finding that makes regeneration more practical using existing HVAC hardware. A double layer of ACF cloth shows improved performance for all VOCs, but most critically it results in a doubling of the removal efficiency for formaldehyde. To facilitate deployment of the air cleaning systems in existing buildings, including those with roof-top systems, we developed a conceptual design for an air cleaner that is connected to the ductwork of an existing HVAC system.

Manganese Oxide Catalyst System.

The following sections summarize progress in evaluations of a manganese oxide catalyst applied to particle filters to break down formaldehyde under room temperature conditions. The formaldehyde is converted to carbon dioxide and water vapor.

Scaling Up Methods of Catalyst Production and Application of Catalyst to Particle Filters.

Manganese oxide catalyst production volume has been scaled up to 100 times the initial synthesis volume in the laboratory. A spray coating technique for applying the LBNL-developed catalyst with highest efficiency (called "LBNL-100") to typical fibrous particle filters has been developed and tested. For application of the catalyst to particle filters, a powder-coating gun with a powder reserve (69-207 kPa, powder coating system, Chicago Pneumatic) was procured. The reserve tank of the powder coating system was filled with the LBNL-100 catalyst and fitted to the laboratory air-handling unit. The inlet air to the reservoir was pressurized to 100 kPa to obtain uniform particle size during spraying. The particulate filter to be coated with the catalyst material was fitted in a duct system enabled with a fan/blower. This allowed for the air to be pulled through the filter when the catalyst was sprayed onto the filter. A series of HEPA filters were fitted downstream of the particulate filter media and before the fan, to trap and recover excess catalyst. After each coating, the direction of airflow through the filter was reversed to remove any weakly-attached catalyst from the surface. Each filter media was weighed before and after the coating to obtain the total mass of catalyst deposited on the filter surface, which was typically in the range 3-4 g-m$^{-2}$. The spray application process could easily be automated so that minimal labor is required.

We conducted tests to assure that the catalyst stays attached to the particle filter and is not entrained into the air stream causing potential occupant exposures to suspended particulate matter. Manganese oxides are a common constituent of the earth's crust minerals and urban dust, and exposure of humans to manganese oxides present in the environment is a common occurrence. Reports of long-term occupational exposure to high levels of manganese oxide particles resulting from welding suggest a possible association with health effects. Based on those exposures, the California Office of Environmental Health Hazard Assessment (OEHHA) established a reference level for inhalation exposure of manganese-containing compounds of 0.2 μg-m$^-$$_3$. We performed two different tests to provide a first-order evaluation of potential exposures to airborne manganese caused by use of filters loaded with LBNL-100 catalyst. The first test involved the analysis of particulate matter collected on a 0.2 μm (pore size) Teflon filter that sampled air downstream of the fibrous filter loaded with the LBNL-100 catalyst (face velocity through the catalyst-loaded filter was 0.5 m-s$^{-1}$). We did not detect manganese on the downstream filter. The limit of detection for Mn was 0.02 ng-m$^{-3}$, several orders of magnitude below the California Office of Environmental Health Hazard Assessment (OEHHA) inhalation exposure levels. The other test performed was a gravimetric determination of catalyst loss from the substrate after it had been used to remove formaldehyde for more than 40 days at a face velocity of 50 cm-s$^{-1}$. The difference in filter weight before and after reaction was below the detection limit (<0.1 mg), showing undetectable loss of the catalyst. Both preliminary tests suggest that catalyst particles do not significantly enter the airstream that passes through the filter.

We have also scaled up this test for catalyst coated filters to be deployed in the field. The air velocity through a catalyst-coated filter was maintained at 1 m-s$^{-1}$. Upstream and downstream particle samples were collected for a period of 24 hours using 0.2 μm (pore-size) Teflon filter at a sampling rate of 1 L-m$^{-1}$. The particles were analyzed using ICP-MS. The net Mn concentration downstream was lower than that observed upstream indicating that the catalyst was not released from the filter into the airstream, and that, instead, the filter removed naturally-occurring particles containing Mn.

Effect of Humidity on Catalyst Performance.

Figure 8:
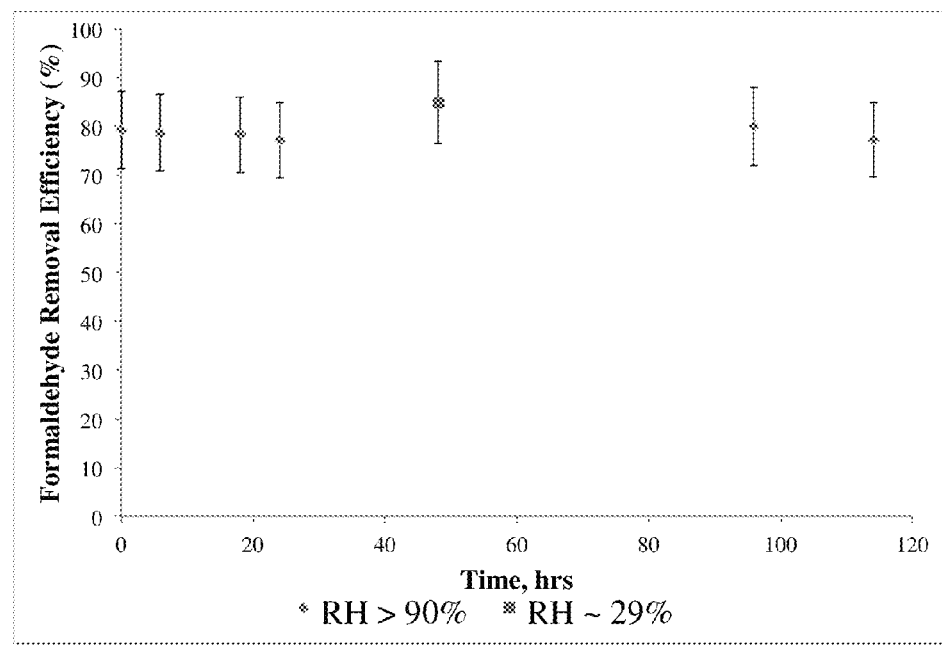
FIG. 8 shows formaldehyde removal performance of laboratory synthesized manganese oxide catalyst for different RH conditions.

Studies of the effect of humidity on the manganese oxide catalyst synthesized in the laboratory showed promising results. The filter loaded with manganese oxide was tested using an airstream saturated with water for a period of 100 hours at a face velocity of 0.5 m-s$^{-1}$. FIG. 8 shows the results obtained for the experiments conducted at near saturation humidity conditions. The formaldehyde removal efficiencies at near-saturation humidity were slightly lower than the formaldehyde conversion at 25-30% RH reported previously (Sidheswaran, M. A., H. Destaillats, D. P. Sullivan, and W. J. Fisk. 2010. New air cleaning strategies for reduced commercial building ventilation energy. *LBNL-4026E Report*. Lawrence Berkeley National Laboratory, Berkeley, Calif., USA) where efficiencies were as high as 85-90%. When the humidity in the system was reduced back to 29% RH, the removal efficiency of formaldehyde increased to 80% to 85% showing the ability of the catalyst to regenerate at a lower humidity. The slight decrease in formaldehyde removal efficiency at higher humidity conditions might be attributed to the competitive adsorption of water on the surface of the catalyst.

Effect of Filter Tackifier on Catalyst Performance.

We also studied whether the performance of the catalyst was affected by the adhesives or tackifiers that are present on some commercially available filters. Previous studies by Destaillats et al. (Destaillats, H., W. Chen, M. G. Apte, N. Li, M. Spears, J. Almosni, G. Brunner, J. Zhang, W. J. Fisk (2011). Secondary pollutants from ozone reactions with ventilation filters and degradation of filter media additives. *Atmos. Environ.* 45, 3561-3568) have reported that some filters coated with tackifiers can be a source of formaldehyde in the presence of humidity. These oily coatings are applied on filter surfaces to improve the performance of the filter in trapping particulate matter. We tested three different catalyst-coated filters with heavy, medium and mild applications of tackifier. Approximately 3 mg of the same manganese oxide catalyst material was coated on 10 $cm^2$ filter surfaces on all three types of filters. The filters were fitted in the experimental setup used in our FY10 studies (Sidheswaran et al., 2010). The formaldehyde inlet concentration was maintained at ~70 ppb and the face velocity was ~0.75 m $s^{-1}$.

Figure 9:
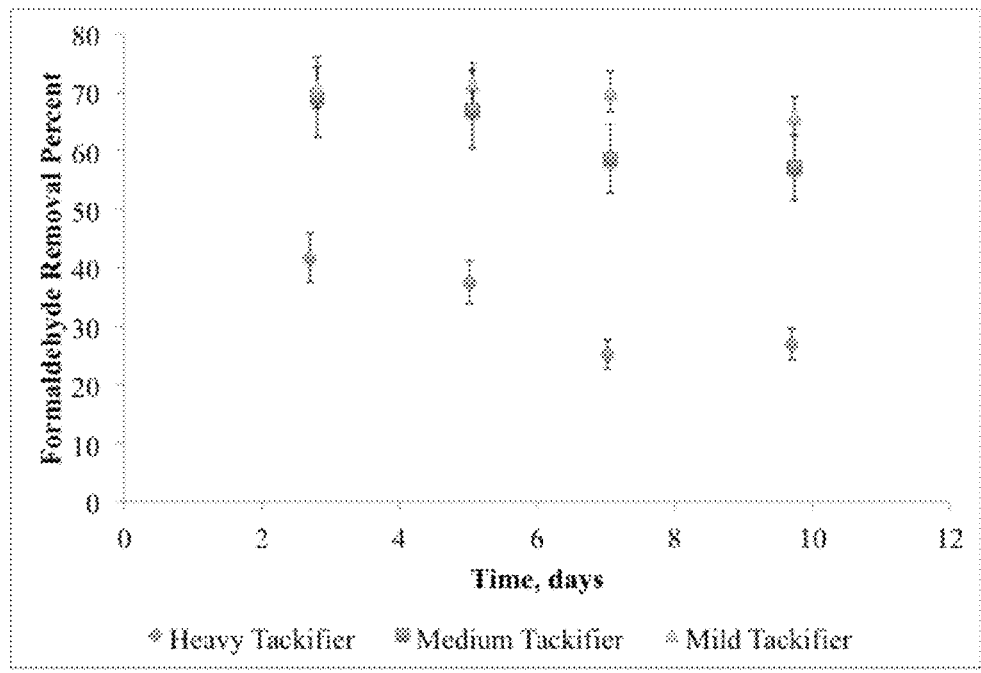
FIG. 9 shows performance of manganese oxide coated filters with different tackifier loading.

FIG. 9 shows the plot of formaldehyde removal vs. time for manganese oxide coated filters with different tackifier loadings. It was found that tackifier loading on the filter surface has an important effect on formaldehyde removal efficiency. The catalyst-coated filter with lower or medium tackifier loading performed significantly better than the catalyst coated filter with heavy tackifier loading. It should be noted that although the performance of the filter with heavy tackifier coating was not as impressive as the other filters, it is still far better than a similar filter without any catalyst coating. Currently long term tests are being carried out with this system to evaluate the lifetime of the catalyst.

Long Term Performance of the Catalyst.

Long term $MnO_x$ tests of the catalyst are underway and we have obtained encouraging results so far. The experimental setup is similar to that described in next section. We are currently testing the catalyst applied to a filter system with mild tackifier loading. Room air is drawn at a flow rate of 30 L $min^{-1}$ through a 4-L stainless steel source chamber containing a 25 cm by 10 cm cabinetry specimen, which serves a strong formaldehyde source. Characterization of this diffusive source was performed in a previous study at our laboratory (Maddalena, R., M. Russell, D. P. Sullivan, and M. G. Apte. 2009. Formaldehyde and Other Volatile Organic Chemical Emissions in Four FEMA Temporary Housing Units. *Environmental Science & Technology*. 43: 5626-5632). The 10 $cm^2$ filter sample loaded with 3 mg of LBNL-100 $MnO_x$ catalyst was placed downstream of the stainless steel chamber. VOC and formaldehyde samples upstream and downstream were periodically collected using DNPH and Tenax sorbent tubes.

Figure 10:
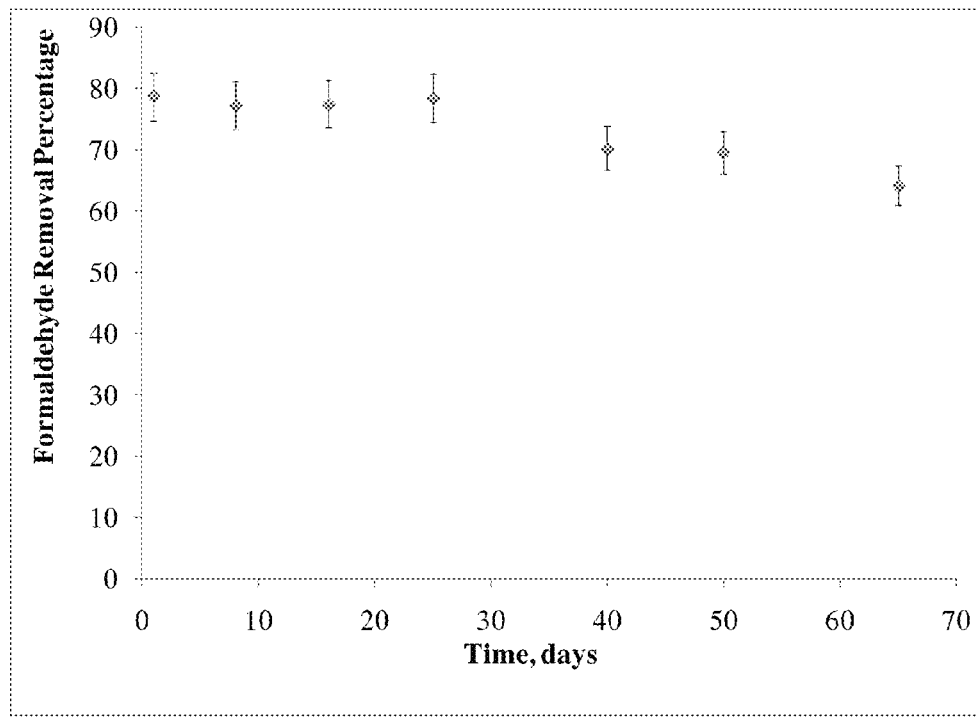
FIG. 10 shows performance of manganese oxide coated filter for a period of 65 days.

FIG. 10 shows the formaldehyde removal efficiency of the LBNL-100 catalyst for a period of 65 days. The formaldehyde removal efficiency of the catalyst decreased from 80% to about 64%. There may be several factors leading to the decrease in efficiency. The HVAC filter has a mild loading of tackfier oils that may degrade catalyst performance. Also, over time, airborne particles are accumulating on the filter surfaces and these particles may limit access to the catalyst's active sites. We also measured particle number concentration upstream and downstream the filter in our experimental setup to estimate particle accumulation on the surface of the filter. We found that the number concentration decreased from ~4000 # $cm^{-3}$ to 1500 # $cm^{-3}$ showing accumulation on the surface of the filter. This also supports the reason for decreased performance of the LBNL-100 coated filter continuously operated over a period of 65 days. However, a continuous operation for 65 days corresponds to 130 days of filter deployment in a commercial building with 12 hours per day of HVAC operation, and most filters are replaced within or before 130 days of filter deployment. Also, the catalyst could be applied to a set of filters, protected by upstream pre-filters. The use of pre-filters and subsequent downstream filters is a common practice. Finally, it should be pointed out that, even though performance decreased in the studied period, the final removal efficiency (64%) was still remarkably high.

Deployment of the Catalyst as Paint Additive for Passive Air Cleaning Applications.

We explored the possibility of using manganese oxide catalyst in paint or primer as a passive technology to remove formaldehyde from indoor air. We mixed ~10 mg of manganese oxide LBNL-100 in 250 ml of primer (VOC free, Mythic tint base) and 500 ml of paint (VOC free Mythic semi-gloss enamel) and prepared four different painted surfaces with the catalyst added to the paint and/or primer. Case 1 used $MnO_x$ in primer plus normal paint, Case 2 used $MnO_x$ in both primer and paint, Case 3 used normal primer and $MnO_x$ added to paint, and Case 4 used normal paint and normal primer. Paint testing charts (Leneta Form1B Penopac Chart) were used as substrates for testing the paint samples. The testing charts were weighed before and periodically after painting to obtain a steady mass of painted sample. This was performed for all samples to account for the volatile losses from the paint. One unpainted chart was also tested as an experimental blank. The details of the paint samples and the weights are listed in Table 5. The samples were then introduced in five different experimental test cells to evaluate the formaldehyde removal capabilities of manganese oxide paint and primer samples. The experimental setup is shown in FIG. 4. A 2 ml amber vial containing 5% formalin solution was used as the formaldehyde source and placed inside a 200 L chamber. After the experiment was run for 10 days, we decided to implement a step change in formaldehyde concentration to saturate the paint samples and the substrate (Leneta chart). The 5% formalin solution was replaced with 37% formalin solution to achieve this step change. The formaldehyde concentration was restored in the system after a period of 5 days to the original value of 20-30 ppb. House air was connected to the chamber inlet and pulled through the test cells at the rate of 0.2 L-$min^{-1}$ resulting in a residence time for air comparable to that in a room (20 min). Dinitrophenylhydrazine (DNPH) cartridges were used to collect upstream and downstream air samples to measure formaldehyde concentration in the flow cells. DNPH cartridges were extracted with 2-mL aliquots of acetonitrile, and the extracts were analyzed by HPLC with UV detection at $\lambda_{max}$=360 nm (Agilent 1200). A calibration curve for quantification was carried out using authentic standards of the formaldehyde-DNPH hydrazone.

TABLE 5

Mass of paint and primer applied to substrate.

| Sample ID | Sample Type | Mass of Paint and primer applied (g) |
|---|---|---|
| Case 1 | Paint on Primer | 7.2 |
| Case 2 | Paint on $MnO_x$ Primer | 7.6 |
| Case 3 | $MnO_x$ Paint on Primer | 10.3 |
| Case 4 | $MnO_x$ Paint on $MnO_x$ Primer | 10.4 |
| Case 5 | No Paint | — |

Figure 11:
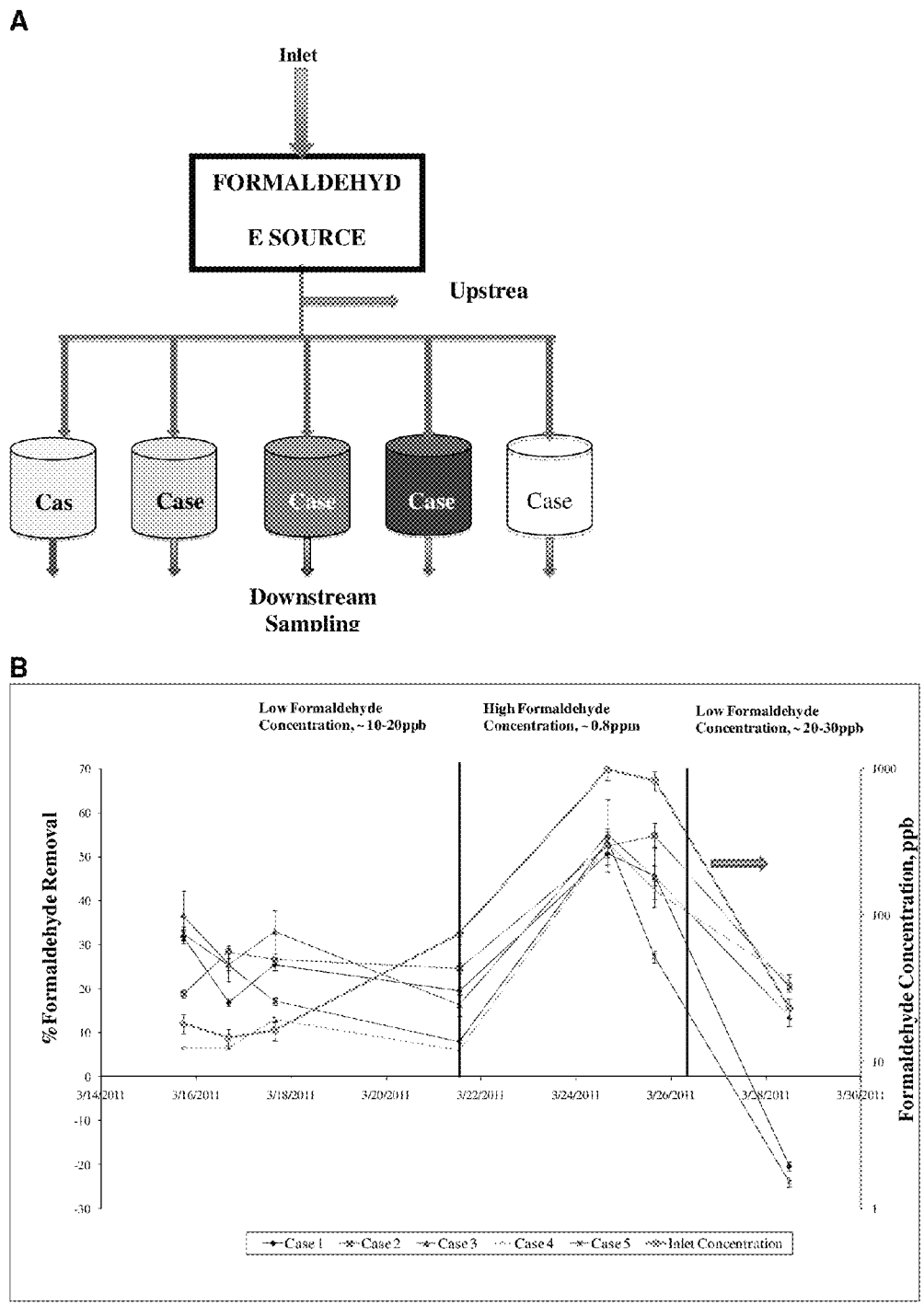
FIG. 11 shows (A) an experimental system for evaluation of formaldehyde removal by paints mixed with manganese oxide catalyst, and (B) formaldehyde removal efficiency of painted samples with and without catalyst.

The initial experimental results obtained from these experiments are shown in FIG. 11. The white color of paint and primer changed considerably after manganese oxide was added. The inlet concentration to all of the flow cells was monitored and the concentration was maintained at ~20 ppb. The Leneta chart substrate and the paint show initial formaldehyde removal, possibly by simple adsorption. When the inlet concentration was increased 40-fold, the formaldehyde removal efficiency of the samples increased to ~50%. The samples Case 2, Case 3, and Case 4 showed improvement in their performance with time. An average of removal of 25-30% was seen for all samples. Sample Case 2, which is paint on manganese oxide coated primer performs moderately compared to the other manganese oxide coated samples. The comparatively low performance of manganese oxide catalyst in paint could be attributed to multiple factors. The pore structure and the surface area of the catalyst may be altered when mixed in paint or primer.

Field Study of $MnO_x$-Coated HVAC Filters in a Small Commercial Building.

A field study is currently underway to better assess the potential benefits of $MnO_x$-coated HVAC filters. A small commercial office building that had been characterized in a previous study at our group was selected to conduct this task, because it combined two key features: relatively high formaldehyde levels and a single-filter HVAC unit. The indoor formaldehyde concentration in that office building was determined in the previous study to be ~35 ppb. The primary ventilation source to the building was reported to be through the HVAC system as the single entrance door was predominantly kept shut, making this an ideal candidate for testing the catalyst coated filters. The field test is being conducted over a period of several consecutive weeks during which we alternate between a filter without catalyst and a catalyst-treated filter placed in the HVAC system. Concentrations of formaldehyde upstream and downstream of the filter, in the indoor air, and in outdoor air are monitored. Temperature and humidity are logged and a passive tracer gas method is used to measure ventilation rates. At this time, we have installed the instrumentation and initiated collection of data. The formaldehyde concentration indoor was observed to be ~45-50 ppb. The outdoor formaldehyde levels were less than 3 ppb. The formaldehyde concentration in the office space was thus due to significant indoor sources. A 51 cm by 63.5 cm by 2.54 cm deep pleated air filter (ACE 4045134) was coated with LBNL-100 $MnO_x$ catalyst with a loading of 4 g $m^{-2}$. An identical non-catalyst coated filter was replaced with the catalyst-coated filter and the formaldehyde concentration was monitored in the office space. After 20 hours, the concentration of formaldehyde in the room was reduced from approximately 48 ppb to 6 ppb. The face velocity across the filter was estimated to be 2 m $s^{-1}$ and the room had no evident outdoor ventilation system. When the catalyst-treated filter was replaced with the untreated filter, the formaldehyde concentration increased back to approximately 50 ppb.

Evaluations of Activated Carbon Air Cleaning with In-Situ Regeneration.

LBNL initiated studies of the use of activated carbon fiber (ACF) cloth media for VOC air cleaning. The ACF media is placed in an airstream and physically adsorbs a broad range of VOCs, yielding air with lower concentrations of VOCs that is supplied to the occupied spaces of a building. Periodically, the flow of air delivered to occupied spaces is stopped, and the ACF media is regenerated by passing heated or unheated outdoor air through the ACF media in order to drive off the previously adsorbed VOCs, which are vented outdoors. The air cleaning process is then restarted. This technique can be effective for a broad range of VOCs, but has a lower effectiveness for formaldehyde, a compound that is too volatile to be retained with high efficiency by sorbent media. With heating of the ACF media, the regeneration flows can be as low as 1% of the flow rate during air cleaning, with a regeneration period of 15 minutes each 12 hours. The energy required for regeneration is small relative to the energy needed to condition outdoor air that provides an equivalent amount of indoor VOC removal.

Impact of High Face Velocity.

Details of the experimental setup and electrothermal regeneration methods can be found elsewhere (Sidheswaran et al., 2010). In electrothermal regeneration, the activated carbon is heated by passing an electrical current through the ACF media. Two different face velocities, 0.75 m $s^{-1}$ and 1.0 m $s^{-1}$ were used to evaluate the performance of ACF at elevated face velocities. The pressure drop across the ACF cloth was periodically monitored during these runs. Before we subjected the cloth to periodic adsorption and regeneration, the cloth was conditioned at 150° C. for 15 hours. The ACF filters were saturated with a list of model VOCs for a period of 105 hours. The physical properties of the VOCs used in this study can be found in other previous reports (Sidheswaran et al., 2010). In the results reported here, one cycle refers to a 12 hour adsorption period followed by a 15 minute electrothermal regeneration period at 150° C. at 1/100th face velocity used during air cleaning.

Figure 12:
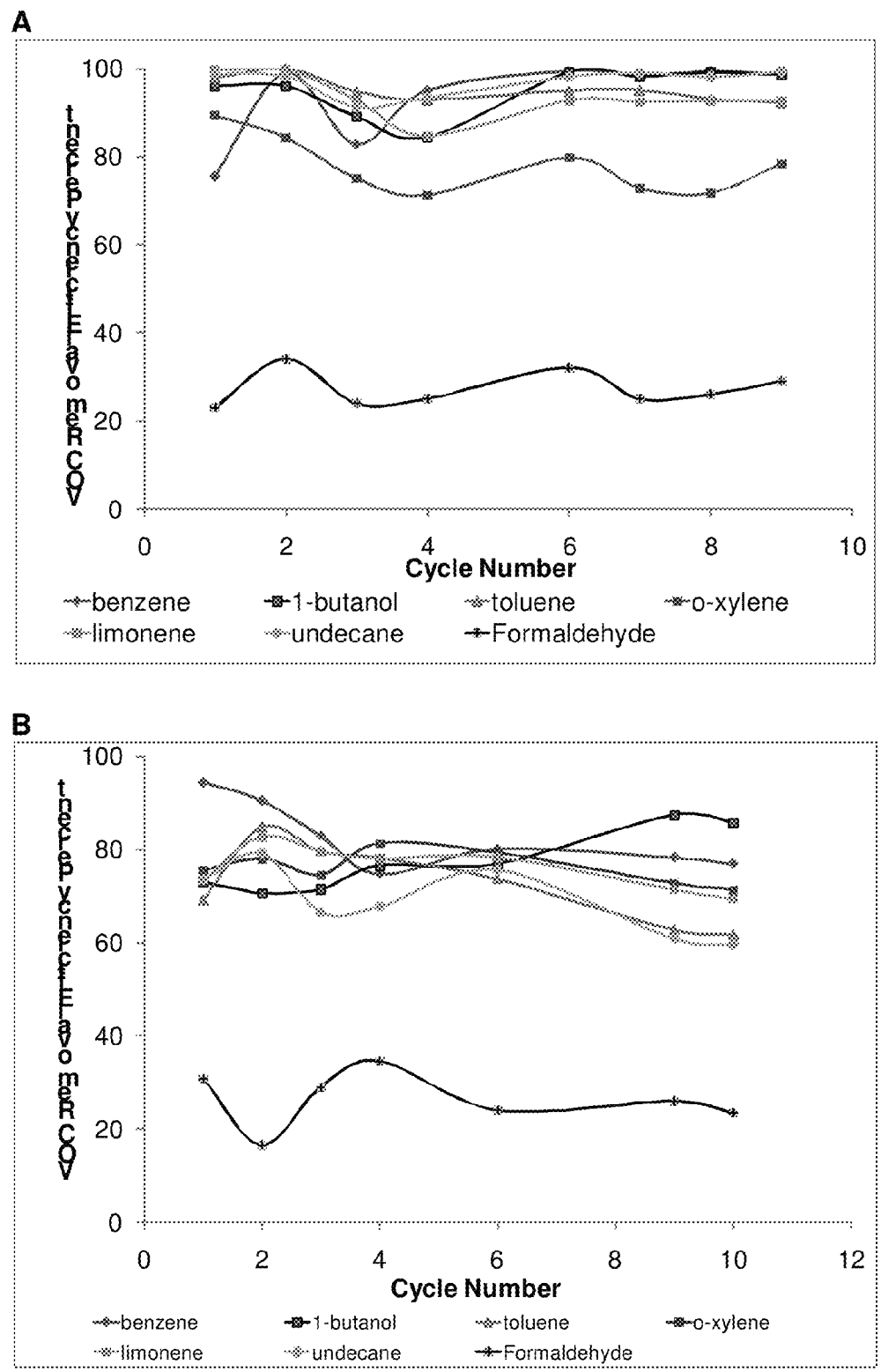
FIG. 12 shows VOC removal efficiency of ACF at (a) face velocity of 0.75 m s$^{-1}$, (b) face velocity of 1.0 m s$^{-1}$.

FIGS. 12 (A) and (B) show the VOC percent removal for different organics at a face velocity of 0.75 m $s^{-1}$ and 1.0 m $s^{-1}$ respectively. The pressure drop across the ACF was measured to be ~78 Pa and 98 Pa for each of those conditions. These pressure drop values are comparable to those of relatively low efficiency unused particulate filters, hence making these cloths suitable for operation under high face velocity regimes. For both face velocities of 0.75 m-$s^{-1}$ and 1.0 m-s an average formaldehyde removal efficiency of ~25% was achieved which is comparable to what was found earlier (Sidheswaran et al., 2010) for lower face velocities. The o-xylene removal efficiency of the carbon cloth for the face velocity of 0.75 m $s^{-1}$ was found to be between 70 and 80% while that of other compounds such as benzene, toluene, limonene and 1-butanol were found to be consistently above 90%. At the higher face velocity of 1 m $s^{-1}$ the VOCs other than formaldehyde had average removal efficiencies ranging between 70-80% with very high initial removal rates. The better performance of the ACF cloth can be attributed to shorter loading cycles. From the previous study at 0.5 m $s^{-1}$ face velocity (Sidheswaran et al., 2010) it was inferred that prolonged operation of the cloth at such conditions may lead to a marginal decrease in performance.

Use of Multi-Layer ACF Cloth System.

In these tests, we evaluated the use of two layers of ACF cloth, with a second layer placed immediately downstream of the first layer. We hypothesized that a double layer system would have a sufficiently high VOC removal efficiency, including for formaldehyde, with high air velocities to make it possible to deploy ACF filters with limited pleating that are 5 cm deep or less. The experimental methods are the same as those described earlier (Sidheswaran et al., 2010). Two layers of ACF cloth ACF were fitted in a filter holder system and subjected to continuous adsorption and regeneration cycles. An adsorption-regeneration cycle in this experimental section refers to a 12 hour VOC adsorption (air-cleaning) period at a face velocity of 0.5 m s$^{-1}$ followed by a 12 hour room temperature ACF regeneration period at a face velocity of 0.005 m s$^{-1}$. We used ambient unheated air regeneration methods to regenerate the ACF cloth pieces.

Figure 13:
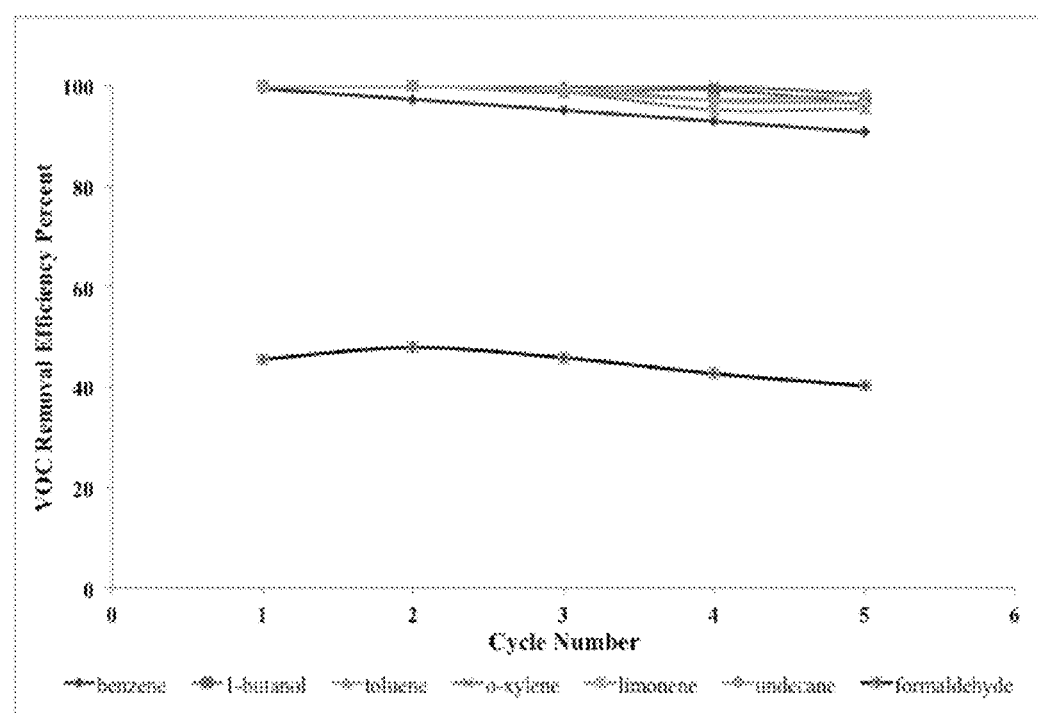
FIG. 13 shows VOC removal efficiency of multi-layered ACF.

FIG. 13 shows the VOC removal efficiency performance of double layered ACF cloth. We monitored the pressure drop across the ACF cloth and it was found to be 93.9 Pa. Although the pressure drop is higher than usual pressure drops across single ACF cloth systems, the multi layered ACF shows consistent good performance even with room temperature regeneration using outdoor air. Also, the pressure drop value compares to those observed through unused low-efficiency particle filters. Formaldehyde removal was consistent and it was more than 40%. This removal rate is twice as much as the single layered cloth. As observed in our previous study (Sidheswaran et al., 2010), the efficiency of formaldehyde removal may increase when regenerated by heating. VOC removal efficiency of greater than 95% was observed for all other VOCs. This is a 20-30% improvement over the removal efficiency observed for the single layer cloth. These results are encouraging and suggest that the ACF can be used in multiple layers successfully. The air velocity in these tests is typical of the velocity through media in a 5 cm thick pleated particle filter, thus the results indicate that a the system would be effective, even for formaldehyde with such a filter which required little space in HVAC system.

Evaluation of Regeneration Heating Options.

Figure 14:
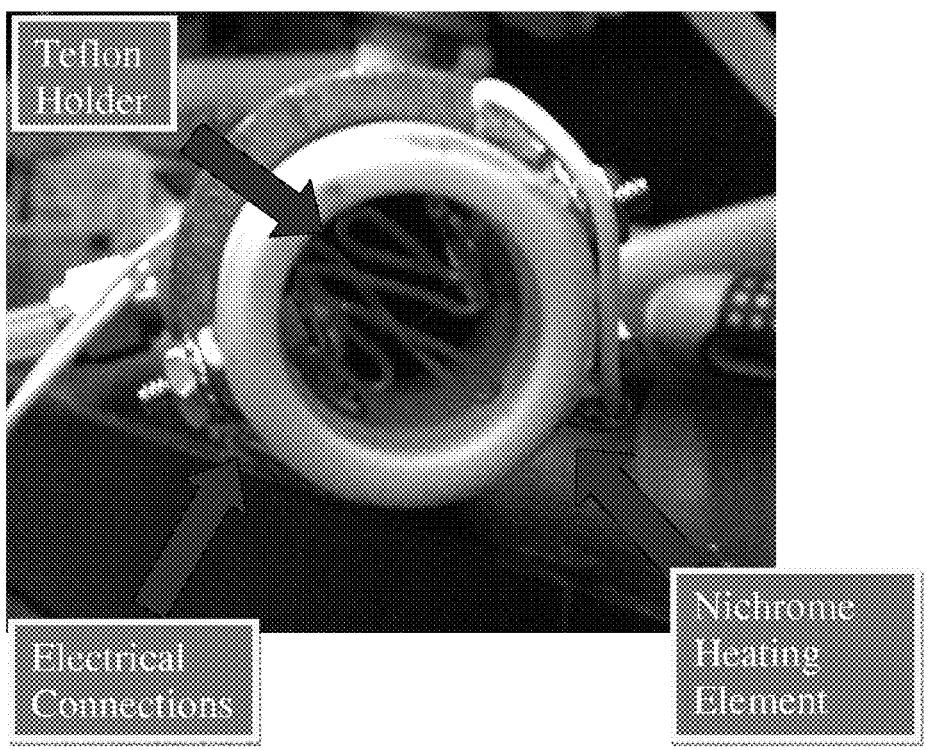
FIG. 14 shows an air heating element for regenerating the ACF.

In our previous experiments, periodic regeneration was achieved by passing an electrical current through the ACF media to reach the desired heating level. However, in large HVAC systems, implementation of the technology by heating the ACF media may not be practical. In these tests, we explored the possibility of instead heating the regeneration air. A heating element was made using Nichrome wire (diameter 0.04 m, length 0.09 m and resistance 0.8 Ω/ft). The wire was weaved inside a Teflon holder and a differential voltage of ~2V was applied across the ends. The heating element is shown in FIG. 14A. The temperature downstream of the ACF media was monitored and recorded using a thermocouple data logger (Extech Easy View 15). The voltage was measured with a multimeter (Keithley 177 Microvolt DMM) and the current across the cloth was measured with an ampmeter. The temperature of the air downstream of the cloth was maintained at 120° C. This yielded a cloth surface temperature of ~150° C., which we measured during initial setup of the heating element. The heating element was placed upstream of the ACF media during regeneration. Hot air was passed through the ACF filter at $\frac{1}{100}^{th}$ face velocity of the adsorption face velocity. The media was regenerated for a period of 15 minutes. The face velocity during adsorption (air cleaning) was maintained at 0.5 m s$^{-1}$. The experimental setup to determine the adsorption efficiency of ACF with heated air regeneration is similar to the procedure employed in previous studies (Sidheswaran et al., 2010). In these experiments, similar to the experiments described on heating the ACF for regeneration, an adsorption-regeneration cycle refers to a 12 hour adsorption period followed by a 15 minute regeneration period with $\frac{1}{100}^{th}$ the air face velocity of adsorption. Before the ACF was subject to periodic adsorption and regeneration cycles, the material was saturated based on the results from the isotherm for a period of 105 hours (Sidheswaran et al., 2010).

Figure 15:
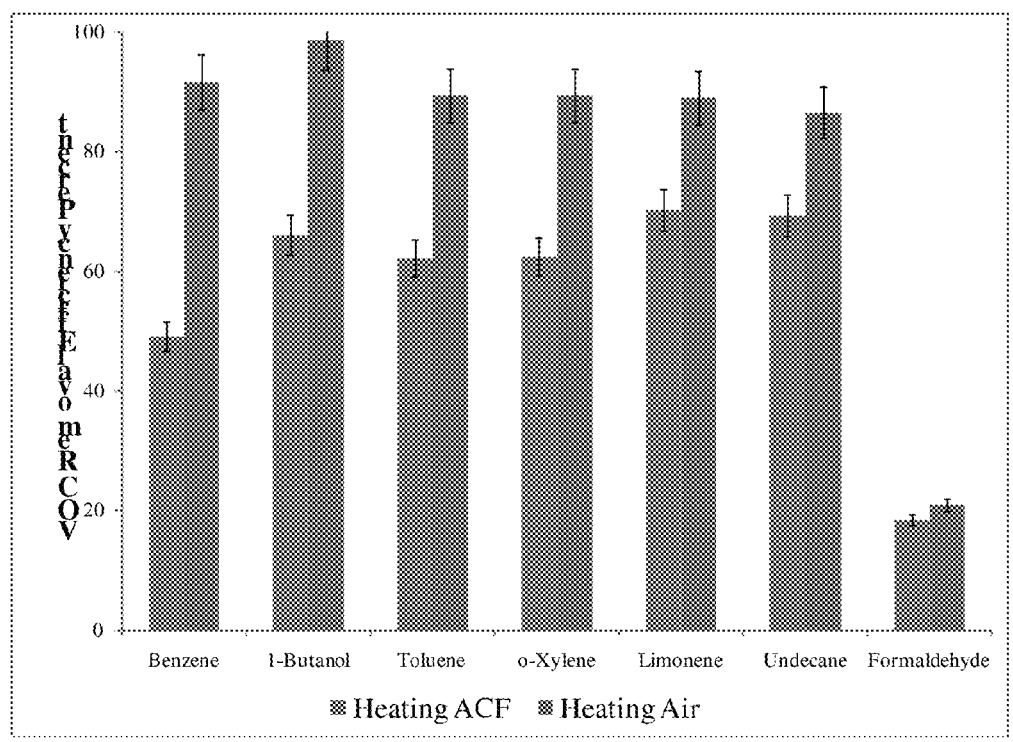
FIG. 15 shows comparison of different regeneration techniques.

FIG. 15 shows the comparison between VOC removal efficiency of ACF at the end of 6$^{th}$ cycle when it was regenerated by heating the ACF with an electrical current and by heating the regeneration air. The ACF that was regenerated by heating the air performed better than the electrically-heated ACF media by about 20-40% for most VOCs except formaldehyde. Both cases show consistent performance. Regeneration by heating the air could prevent the damage of carbon fiber cloth structure and prolong the life of the media unlike when the ACF itself is heated. Also, the method of heating the regenerating air proves advantageous since it is easier to implement in large HVAC systems. It is also possible to successfully recover heat from the exhaust air to minimize energy usage.

The findings of this study were surprising. We expected a similar VOC removal performance when heated air was used for regeneration of the ACF media as opposed to heating the ACF with an electrical current. While we cannot explain the findings, we offer two possibilities. First, we note the difficulties in measuring the temperature of the ACF media during regeneration. To measure the temperature during regeneration, we embedded a small temperature sensor in the ACF cloth, but given the porous nature of the cloth this measurement may not accurately indicate the average temperature of the cloth. Possibly, the average regeneration temperature was higher in the system that regenerated with heated air. Second, we hypothesize that imperfect electrical connections to the ACF cloth when it is regenerated with an electrical current may potentially have led to uneven heating of the ACF media reducing the effectiveness of regeneration.

Evaluation of Direction of Airflow During Regeneration of the ACF Media.

Small-scale tests were performed to determine how ACF regeneration performance compares when the direction of airflow through the ACF media is changed. In theory, regeneration with air flowing opposite of the direction during air cleaning is optimal, but the benefits may be modest. In prior research, the regeneration airflow direction was reverse of the airflow direction during air cleaning. If both airflow directions lead to good ACF performance, deployment options will be increased. The ACF cloths were loaded with VOCs as described in the earlier sections at a face velocity of 0.5 m s$^{-1}$. Heated air was used to regenerate the ACF media at 150° C. with a face velocity of 0.005 m s$^{-1}$ for a period of 15 minutes. The method of regeneration is described in the previous section. In one test system, the airflow direction was the same as that during air cleaning and in a second test system the air flow direction was reversed during regeneration.

Figure 16:
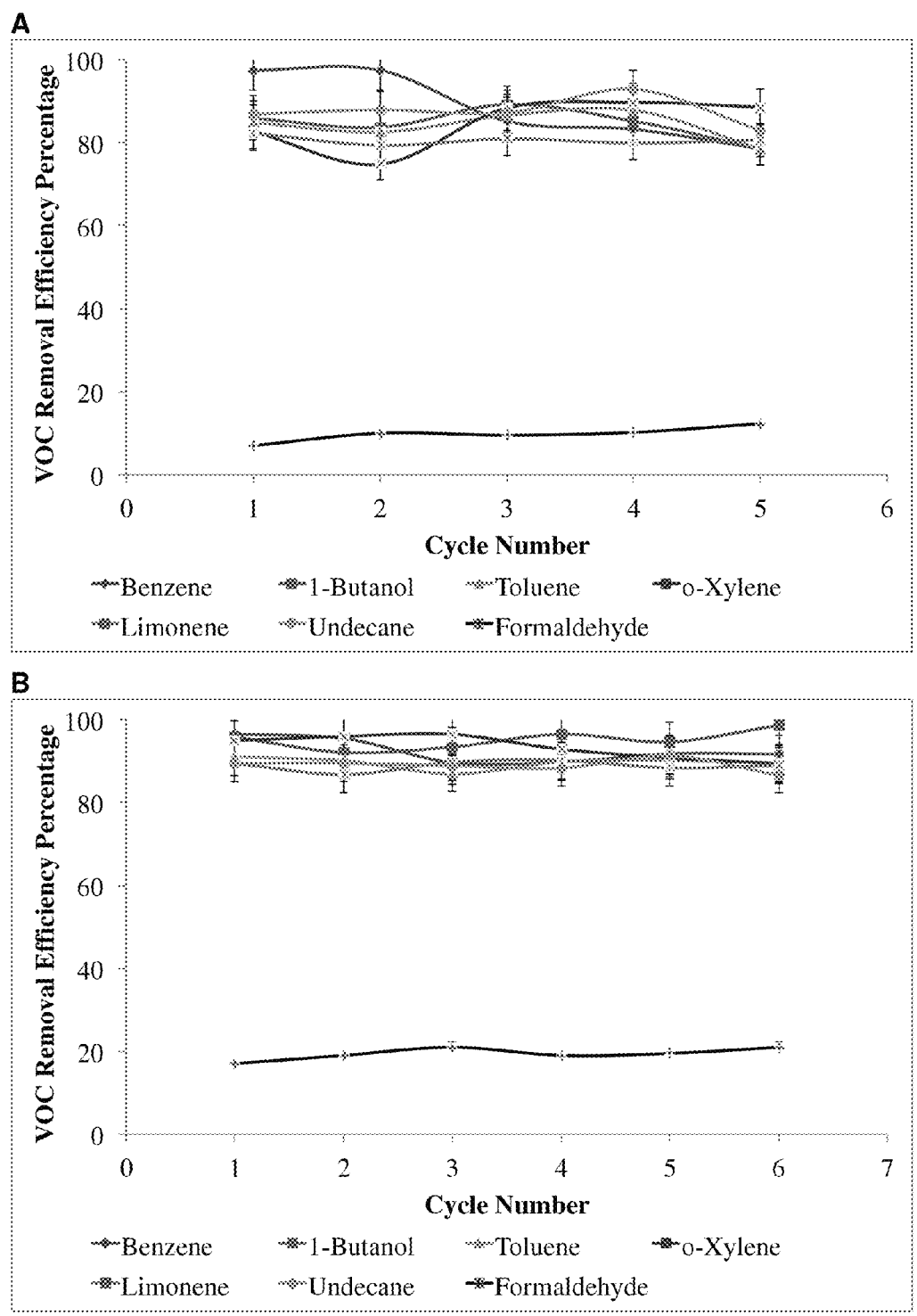
FIG. 16 shows VOC removal efficiency percentage for (A) same direction of air flow during air cleaning and regeneration and (B) opposite direction of air flow during air cleaning and regeneration.

FIGS. 16 (A) and (B) show the VOC removal efficiency percent of the ACF cloths for two different regeneration air flow directions. Better VOC removal performance was obtained when the direction of airflow was reversed during regeneration (FIG. 16B) compared to not reversing the airflow direction (FIG. 16A). However, the variability is less than 15% for most VOCs suggesting that the direction of airflow during regeneration can be in the same direction of air cleaning for practical purposes.

Evaluation of Effect of High Relative Humidity on Adsorption Characteristics of ACF Media.

Figure 17:
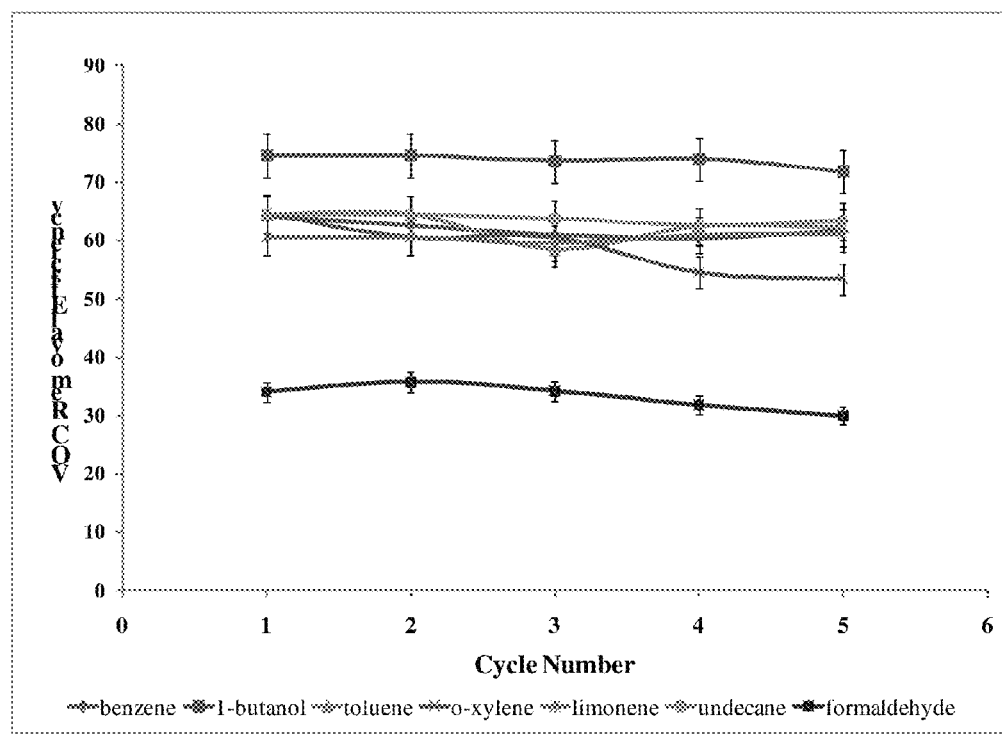
FIG. 17 shows VOC removal efficiency of ACF for 12 hour adsorption cycle at face velocity of −0.5 m s$^{-1}$ with 75% RH and 15 min. regeneration period at 150° C. at a face velocity of 0.005 m s$^{-1}$.

Humidity is another challenge that needs to be addressed when the ACF media is deployed in HVAC systems. Additional experiments were carried out at 75% relative humidity to evaluate the effect of humidity on adsorption of the VOCs by the ACF media. The tests with 75% humidity were conducted for a period of 12 hours with a face velocity of 0.5 m s$^{-1}$ during air cleaning followed by heated regeneration for 15 minutes at 0.005 m s$^{-1}$ face velocity and a temperature of 150° C. Upstream and downstream VOC samples were collected at the end of 12 hours to evaluate the effect of humidity on adsorption capabilities of the carbon fiber in the presence of humidity. The results of the adsorption (air cleaning) experiments with 75% RH and regeneration at 150° C. are presented in FIG. 17. The percent removal of non-polar compounds by the ACF such as benzene decreased by <5% while that of compounds soluble in water such as formaldehyde increased by about 10%. The heated regeneration of the activated carbon was effective in restoring the adsorption properties of the ACF.

CONCLUSIONS

Systems for producing manganese oxide catalyst were scaled up by a factor of one hundred. A convenient spray process was developed for applying catalyst to particle filters. Tests indicate that the catalyst remains attached to the particle filter during subsequent filter deployment. A test indicates that high humidity does not substantially degrade catalyst performance. Experiments determined that heavy layers of tackifier (adhesive) applied to some particle filters can degrade catalyst effectiveness. Experiments to date indicate that the performance of manganese oxide catalyst has diminished by only ~18% after 65 days of continuous use in a typical building, corresponding to 130 days of use in a building with 12-hours per day of HVAC operation. The initial results of a field study of the catalyst system are very encouraging, with approximately 80% reductions in indoor formaldehyde concentrations obtained simply by replacing existing particle filters with catalyst-treated filters. The ACF system retained VOC removal efficiencies above the required levels for all VOCs other than formaldehyde, with air velocities increased by 50% and 100% of the velocity employed in earlier studies. Using heated air to regenerate the ACF media resulted in higher VOC removal efficiencies than regeneration by heating the ACF media with an electrical current. This finding will make regeneration very practical with standard hardware. VOC removal efficiencies were improved, as expected, with a double layer of ACF cloth. Most importantly, the VOC removal efficiency for formaldehyde approximately doubled, resulting in a system that clearly exceed targets for all tested VOCs. Only modest reductions in VOC removal efficiency occurred when the direction of airflow during regeneration was not reversed relative to the airflow direction during air cleaning.

Example 4

A design target for ITAC includes an air flow rate of 47 L/s (100 cfm), a removal efficiency of 70% for a range of VOCs and for 0.3 micrometer size particles, a time-average power consumption less than 50 W. The targeted 47 L/s (100 cfm) airflow and pollutant removal efficiencies are indicated via mass balance modeling to be sufficient to substantially reduce indoor pollutant levels in new houses which typically have air exchange rate of approximately 0.3 h$^{-1}$, or to enable air quality to be maintained in new houses with substantial reductions in outdoor air ventilation rates. An ITAC system with a higher flow rate is a suitable first option. Higher flow rates may be needed in existing houses, which typically have higher air change rates than new houses, and the existing house market is commercially the preferred initial target for a new product. Consequently, a design target for ITAC includes an air cleaner with a 71 L/s (150 cfm) airflow capability and 60 W power consumption.

With the ACF element excluded, the ITAC retains one or more disposable particle filters, at least one filter treated with the manganese oxide catalyst, a fan system, controls, and a cabinet holding the components. Also, the ITAC may optionally incorporate a disposable filter that incorporates traditional granular activated carbon (GAC) or a pad made of traditional activated carbon. Such filters with activated carbon are now widely available, primarily in the commercial building market, for odor control. Our calculations indicate that these commercially available filters do not contain sufficient activated carbon to be effective for VOC control over the duration of filter deployment; however, they can be effective for ozone removal for several months (Fisk, W. J., Spears, M., Sullivan D., and Mendell, M. (2009) Ozone removal by filters containing activated carbon: a pilot study. *Proceedings of the Healthy Buildings* 2009 *Conference*, Syracuse, N.Y., LBNL-4828E). In addition, for VOC removal a disposable filter with GAC may nicely complement a filter treated with the manganese oxide catalyst. GAC has a much higher capacity for retaining high molecular weight VOCs than lower molecular weight VOCs, and GAC is almost entirely ineffective for the most volatile VOCs such as formaldehyde. If an upstream catalyst-treated filter removes most of the VOCs, the amount of GAC in the filter may be sufficient to remove the remaining predominately higher molecular weight VOCs that pass through the catalytic filter. Optionally, an upstream filter containing GAC may pass through most VOCs after a short period of deployment, but still remove the high molecular weight VOCs most likely to shorten the life of the catalyst.

We have identified an existing residential air cleaner with high efficiency fan system (RabbitAir Minus A2; RabbitAir, Pasadena, Calif.) that uses a stack of filters in series. This unit can be modified to incorporate all of the desired filtration elements. This is the only air cleaner identified that uses an energy efficient brushless DC fan motor. It is one of the quietest air cleaners identified. In its original configuration, fan power is about 40 W with a 71 L/s (150 cfm) airflow. This air cleaners can be modified for evaluations in the laboratory and for field studies. Several houses have been screened for VOCs levels and two selected for the field studies. Two of the modified air cleaners have filters in the following order: (1) coarse prefilter/screen, (2) medium filter, (3) HEPA filter, (4) catalyst-treated medium filter. Two additional air cleaners have filters in the following order: (1) coarse prefilter/screen, (2) Tridek C Carbon Impregnated Filter Pad with 345 g of activated carbon per ft2 media, (3) HEPA filter, and (4) catalyst treated medium filter. The coarse pre-filter screen, medium filter, and HEPA filter are provided as original equipment. The catalyst-treated filter is a fiberglass pad filter from American Air Filter (AAF International, Louisville, Ky.) treated with the manganese oxide catalyst. The carbon-impregnated filter pad is a commercial product from Tridek Corp. (TRI-DIM Filter Corporation, Louisa, Va.), cut to size for this application. Other configurations of filter elements are possible, including placement of the filter with activated carbon downstream of the catalyst-treated filter and use of the D-Mark carbon web pad in place of the Tridec C Carbon impregnated filter pad.

The ITAC system can optionally comprise an ACF element that is regenerated in-situ with heated air. In such an embodiment, operating the ITAC comprises periodically stopping the flow of indoor air through the air cleaner, isolating the ACF filter element from indoor air, providing outdoor air for regeneration, heating this air to at least about 150° C., passing the heated air through the ACF media, and venting the VOCs desorbed from the ACF out of the ITAC, such as to outdoors. This system may comprise sections of small-diameter tubes connecting the air cleaner to outdoors. A first tube brings outdoor air to the air cleaner for use in the regeneration of the ACF media and a second tube vents this air plus VOCs desorbed from the ACF to outdoors. For a 71 L/s (150 cfm) air cleaner, a regeneration airflow rate of 0.7 L/s (1.5 cfm) is adequate. Even lower regeneration airflow rates may be effective, but system performance at lower flow rates has not yet been shown. With no heat recovery between the incoming and outgoing regeneration air, and no conductive losses, a 100 W heater, operated 15 minutes per day, is needed. The apparatus holding the ACF cloth must be able to withstand 150° C. temperatures.

Figure 18:
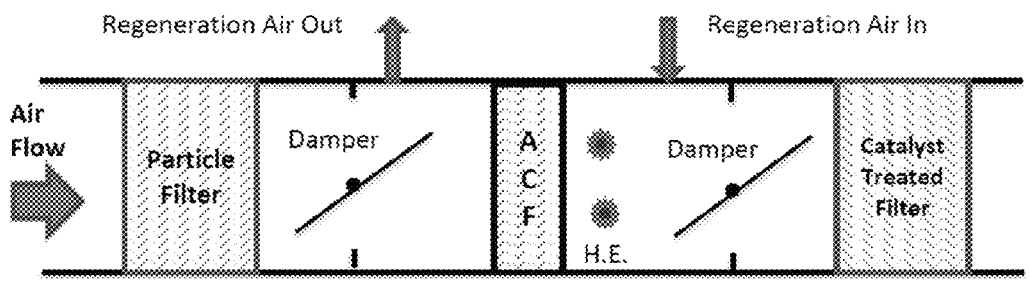
FIG. 18 shows an integrated-technology air cleaner (ITAC) design. "H.E." is the heating element for regeneration.

An embodiment of the ITAC is shown in FIG. 18, with optional electrically actuated dampers located upstream and downstream of the ACF element. These dampers close and isolate the ACF media from the indoor air during the regeneration cycle and are able to withstand 150° C. temperatures. Such a damper system is technically feasible and practical, such as in larger commercial building applications.

Figure 19:
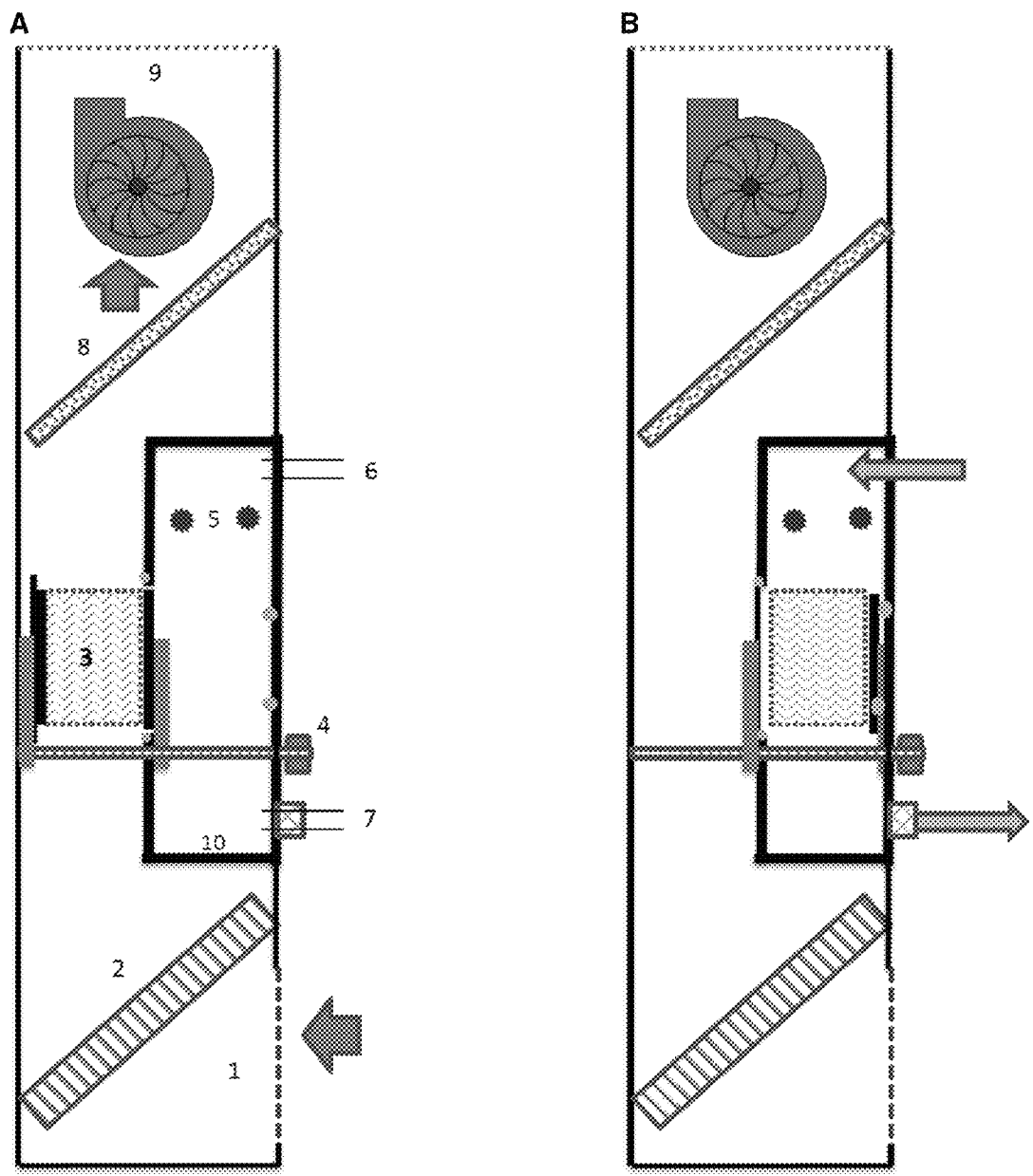
FIG. 19 shows a cross-section view of an embodiment of the ITAC system configuration with an ACF filter element; wherein 1=inlet screen, 2=high efficiency particle filter, 3=ACF filter unit, 4=screw drive and motor actuator for ACF unit, 5=regeneration air heater lamps, 6=regeneration air inlet, 7=regeneration air outlet and fan, 8=catalyst treated filter, 9=fan, and 10=double-wall insulated perimeter of regeneration air heated chamber.
Figure 20:
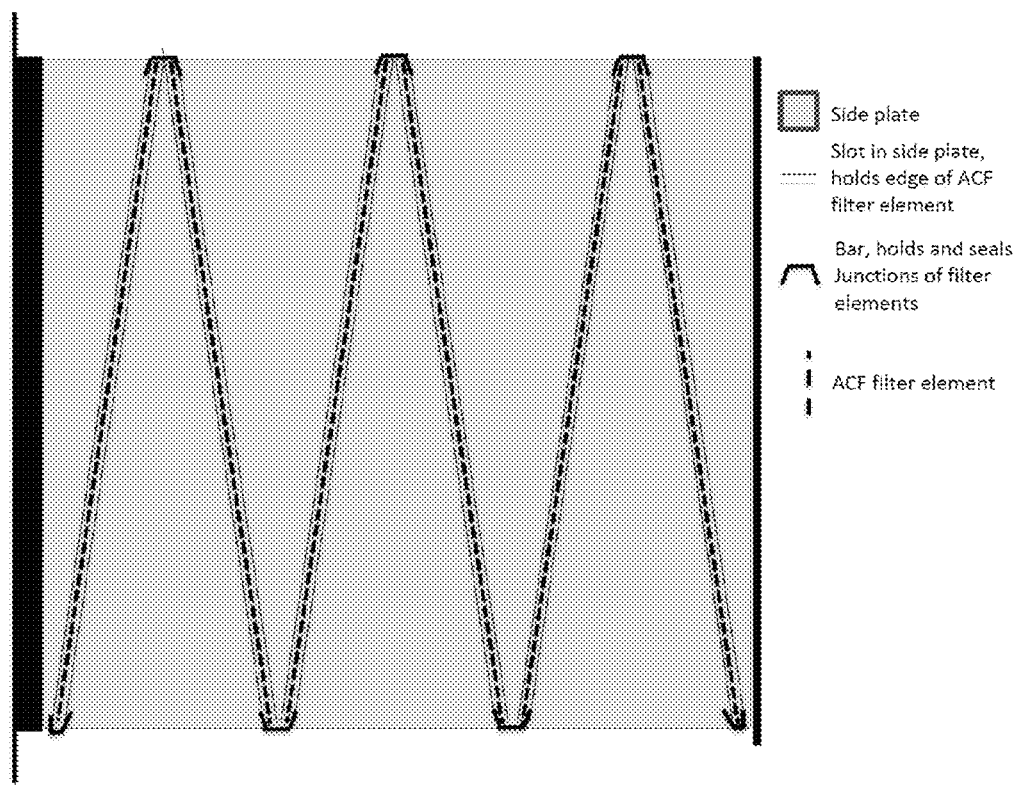
FIG. 20 shows a cross-section view of an embodiment of an ACF filter box.
Figure 21:
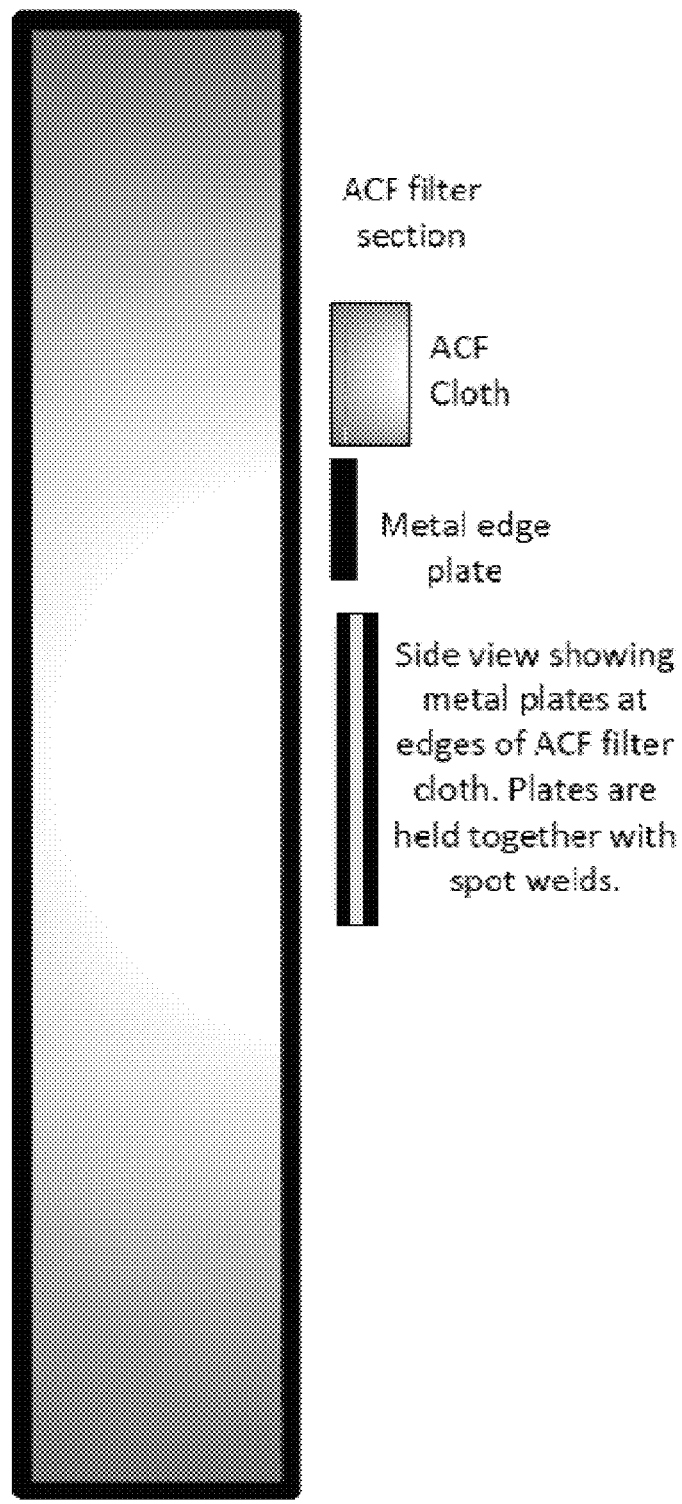
FIG. 21 shows an ACF filter section.

Given the high cost of damper actuators and dampers able to withstand 150° C. temperatures, another embodiment of the ITAC system comprises a moveable ACF filter box. With this embodiment only one screw-type or linear actuator is required, seals that withstand high temperatures and isolate the ACF unit from indoor air during regeneration cycles are straight forward, and the heated regeneration section is well isolated from the remainder of the air cleaner and more easily thermally insulated. FIG. 19 shows a cross section of the system configuration, with the ACF filter element shown in the position for air cleaning on the left and the ACF filter element in the position for regeneration on the right. Not shown in this schematic is a simple heat exchanger for preheating the incoming regeneration air with the outgoing regeneration air. In a particular embodiment, the system lacks the connections to outdoors and the VOCs in the heated regeneration air stream are eliminated by passing it through a bed of catalyst. In this embodiment, a HEPA filter and high efficiency fan system, such as from the Rabbitair Minus A2 air cleaner or equivalent products, are employed. The heating elements needed for regeneration can be simple light bulbs used in residential ovens. The few seals required can be made of one or more Viton polymer (DuPont, Wilmington, Del.), which is capable of withstanding high temperatures and is not a significant pollutant source. In one embodiment, the air cleaner cross sectional dimensions can be about 0.46 m by 0.46 m (1.5 ft by 1.5 ft). The filter treated with catalyst can be a fiberglass pad filter from American Air Filter or a low efficiency 2.5 cm (1 inch) thick pleated filter. The moving and heat-resistant ACF filter system is the most complex element of the design. FIG. 20 shows one potential configuration for this unit with ACF filter sections that slide into slots of a metal filter box. Not shown are the drawer slides at each end of the filter box, that support the box and guide its movement. These drawer slides, sometimes used in file cabinets, employ rows of ball bearings in track systems to ease and guide the linear back-and-forth movement of a drawer. The ACF filter sections shown in FIG. 21, are simple sections of ACF cloth, sandwiched between upper and lower perimeter metal frames, with the upper and lower sections of frame held together by spot welds.

ITACs based on such designs can be evaluated in the laboratory under controlled conditions to assess VOC and ozone removal, and be deployed in houses. Indoor VOC, particle, and ozone levels in the house air can be monitored with the air cleaners operating and not operating. Additionally, concentrations of VOCs and ozone at the air cleaner inlet and outlet can be monitored to enable tracking of pollutant removal over time. The systems can be configured such that the filter containing GAC is installed downstream of the catalyst treated filter (currently located upstream).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for reducing formaldehyde content of a gas, comprising:
    at room temperature, contacting the formaldehyde-containing gas with a manganese containing catalyst consisting essentially of nsutite and cryptomelane particles having a Brunner Emmet and Teller (BET) surface area of at least 100 $m^2$ $g^{-1}$, thereby obtaining a gas having a reduced formaldehyde content as compared to the gas before contacting it with the manganese containing catalyst.

2. The method of claim 1, wherein the manganese containing catalyst is a mixture of about 95% nsutite and about 5% cryptomelane.

3. The method of claim 2, wherein the manganese containing catalyst particles have crystallite sizes of about 4 to 10 nm.

4. The method of claim 3, wherein the manganese containing catalyst is a powder comprised of nanospherical particles with diameter smaller than 50 nm.

5. The method of claim 4, wherein the nanospherical particles are monodisperse.

6. The method of claim 4, wherein the nanospherical particles are porous.

7. The method of claim 1, wherein the manganese containing catalyst is formed by a method comprising:
    providing a manganese salt and a permanganate salt solution wherein the molar ratio of the permanganate to manganese salt has a ratio of about 2:3,
    forming a black suspension comprising a precipitate,
    separating the precipitate from the solution,
    optionally, washing the precipitate,
    heating the precipitate to form the manganese containing catalyst, and
    optionally, converting the precipitate into a powder.

8. The method of claim 1, wherein the manganese containing catalyst is comprised in a composition coated on a building or structure.

9. The method of claim 8, wherein the composition is a paint.

10. The method of claim 1, further comprising flowing the gas at a face velocity of about 0.002 to 0.5 m $s^{-1}$ through a device for reducing the formaldehyde content of the gas, wherein the device comprises the manganese containing catalyst applied to an air filter.

11. The method of claim 10, wherein the air filter is a fibrous particle filter.

* * * * *